(12) United States Patent
Saarma et al.

(10) Patent No.: US 8,034,572 B2
(45) Date of Patent: Oct. 11, 2011

(54) RECEPTOR FOR GDNF FAMILY LIGANDS

(76) Inventors: Mart Saarma, Helsinki (FI); Heikki Rauvala, Helsinki (FI); Maxim Bespalov, Helsinki (FI); Sarka Tumova, Helsinki (FI)

(*) Notice: Subject to any disclaimer, the term of this patent is extended or adjusted under 35 U.S.C. 154(b) by 834 days.

(21) Appl. No.: 11/512,408

(22) Filed: Aug. 30, 2006

(65) Prior Publication Data

US 2008/0057516 A1 Mar. 6, 2008

(51) Int. Cl.
*G01N 33/68* (2006.01)
(52) U.S. Cl. ........................................ 435/7.1
(58) Field of Classification Search ................ None
See application file for complete search history.

(56) References Cited

U.S. PATENT DOCUMENTS

2002/0114780 A1  8/2002  Bankiewicz et al.

OTHER PUBLICATIONS

Airaksinen, M.S., and Saarma, M. (2002). The GDNF family: signaling, biological functions and therapeutic value. Nat. Rev. Neurosci. 3:383-394.
Barnett, M.W., Fisher, C.E., Perona-Wright, G., and Davies, J.A. (2002). Signaling by glial cell line-derived neurotrophic factor (GDNF) requires heparan sulphate glycosaminoglycan. J. Cell Sci. 115:4495-4503.
Cardin, A.D., and Weintraub, H.J. (1989). Molecular modeling of protein-glycosaminoglycan interactions. Arteriosclerosis 9:21-32.
Couchman, J. R. (2003). Syndecans: proteoglycan regulators of cell-surface microdomains? Nature 4:926-937.
Davies, J.A., Yates, E.A., Turnbull, J.E. (2003) Structural determinants of heparan sulphate modulation of GDNF signaling. Growth Factors 21: 109-19. [Abstract only].
Eketjäll, S., Fainzilber, M., Murray-Rust, J., and Ibáñez, C.F. (1999). Distinct structure elements in GDNF mediate binding to GFR alpha 1 and activation of the GFR alpha 1-c-Ret receptor complex. EMBO J. 18:5901-5910.
Gill, S.S., Patel, N.K., Hotton, G.R., O'Sullivan, K., McCarter, R.Bunnage, M., Brooks, D.J., Svendsen, C.N., and Heywood, P. (2003). Direct brain infusion of glial cell line-derived neurotrophic factor in Parkinson disease. Nat. Med. 9:589-595.
Hamilton, J.F., Morrison, P.F., Chen, M.Y., Harvey-White, J., Pernaute, R.S., Phillips, H., Oldfield, E., and Bankiewicz, K.S. (2001). Heparin coinfusion during convection-enhanced delivery (CED) increases the distribution of the glial-derived neurotrophic factor (GDNF) ligand family in rat striatum and enhances the pharmacological activity of neurturin. Exp. Neurol. 168:155-161.
Henderson, C.E., Phillips, H.S., Pollock, R.A., Davies, A.M., Lemeulle, C., Armanini, M., Simmons, L., Moffet, B., Vandlen, R.A., and Simpson, L.C. (1994). GDNF: a potent survival factor for motoneurons present in peripheral nerve and muscle. Science 266:1062-1064. [text and figures in separate files in folder Henderson].
Kinnunen, A., Niemi, M., Kinnunen, T., Kaksonen, M., Nolo, R., and Rauvala, H. (1999). Heparan sulphate and HB-GAM (heparin-binding growth-associated molecule) in the development of the thalamocortical pathway of rat brain. Eur. J. Neurosci. 11:491-502.
Kinnunen, T., Kaksonen, M., Saarinen, J., Kalkkinen, N., Peng, H.B., and Rauvala, H. (1998). Cortactin-Src kinase signaling pathway is involved in N-syndecan-dependent neurite outgrowth. J. Biol. Chem. 273:10702-10708.
Lang, A.E., Gill S., Patel, N.K., Lozano, A., Nutt, J.G., Penn, R., Brooks, D.J., Hotton, G., Moro, E., Heywood, P. et al. (2006). Randomized controlled trial of intraputamenal glial cell line-derived neurotrophic factor infusion in Parkinson disease. Ann. Neurol. 59:459-466.
Leppänen, V.M., Bespalov, M.M., Runeberg-Roos, P., Puurand, U., Merits, A., Saarma, M., and Goldman, A. (2004). The structure of GFRalpha1 domain 3 reveals new insights into GDNF binding and RET activation. EMBO J.23:1452-1462.
Lin, L.F., Doherty, D.H., Lile, J.D., Bektesh, S., Collins, F. (1993). GDNF—a glial cell line-derived neurotrophic factor for midbrain dopaminergic-neurons. Science 260: 1130-1132. [text and figures in separate files in folder Lin].
Lindahl, M., Poteryaev, D., Yu, L., Arumäe, U., Timmusk, T., Bongarzone, I., Aiello, A., Pierotti, M.A., Airaksinen, M.S., and Saarma, M. (2001). Human glial cell line-derived neurotrophic factor receptor alpha 4 is the receptor for persephin and is predominantly expressed in normal and malignant thyroid medullary cells. J. Biol. Chem. 276:9344-9351.
Paratcha, G., Ledda, F., and Ibáñez, C.F. (2003). The neural cell adhesion molecule NCAM is an alternative signaling receptor for GDNF family ligands. Cell 113:867-879.
Paveliev, M., Airaksinen, M.S., and Saarma, M. (2004). GDNF family ligands activate multiple events during axonal growth in mature sensory neurons. Mol. Cell. Neurosci. 25:453-459.
Poteryaev, D., Titievsky, A., Sun, Y.F., Thomas-Crusells, J., Lindahl, M., Billaud, M., Arumae, U., and Saarma M. (1999). GDNF triggers a novel Ret-independent Src kinase family-coupled signaling via a GPI-linked GDNF receptor alpha 1. FEBS Lett. 463:63-66.
Pozas, E., and Ibáñez, C.F. (2005). GDNF and GFR alpha 1 promote differentiation and tangential migration of cortical GABAergic neurons. Neuron 45:701-713. Rauvala, H. (1989). An 18-kd heparin-binding protein of developing brain that is distinct from fibroblast growth factors. EMBO J. 8:2933-2941.
Rauvala, H., Huttunen, H.J., Fages, C., Kaksonen, M., Kinnunen, T., Imai, S., Raulo E., and Kilpeläinen, I. (2000). Heparin-binding proteins HB-GAM (pleiotrophin) and amphoterin in the regulation of cell motility. Matrix Biol. 19:377-387.
Rickard, S.M., Mummery, R.S., Mulloy, B., and Rider C.C. (2003). The binding of human glial cell line-derived neurotrophic factor to heparin and heparan sulfate: importance of 2-O-sulfate groups and effect on its interaction with its receptor, GFR alpha 1. Glycobiology 13:419-426.

(Continued)

*Primary Examiner* — Robert C Hayes
(74) *Attorney, Agent, or Firm* — Arent Fox, LLP

(57) ABSTRACT

The present invention relates to an in vitro method for identifying a molecule, which interferes with the interaction between a glial cell-line derived neurotrophic factor family ligand (GFL) and a heparan sulfate proteoglycan (HSPG), by screening a library of molecules against a matrix anchored complex comprising at least one immobilized glial cell-line derived neurotrophic factor family ligand (GFL) and at least one heparan sulfate proteoglycan (HSPG), wherein the interfering molecule is isolated based on its capacity to replace a glial cell-line derived neurotrophic factor family ligand (GFL) in said anchored complex. The invention also relates to a complex for identifying such a molecule. The invention also relates to methods for preventing or delaying a neurodegenerative process as well as to method for prophylactic treatment or treatment of a disorder in the nervous system.

6 Claims, 11 Drawing Sheets

OTHER PUBLICATIONS

Sariola, H., and Saarma M. (2003). Novel functions and signaling pathways for GDNF. J. Cell Sci. 116:3855-3862.

Tanaka, M., Xiao, H.Y., and Kiuchi, K. (2002). Heparin facilitates glial cell line-derived neurotrophic factor signal transduction. Neuroreport 13:1913-1916.

Trupp, M., Belluardo, N., Funakoshi, H., and Ibáñez, C.F. (1997). Complementary and overlapping expression of glial cell line-derived neurotrophic factor (GDNF), c-ret proto-oncogene, and GDNF receptor-alpha indicates multiple mechanisms of trophic actions in the adult rat CNS. J. Neurosci. 17:3554-3567.

Bespalov, M.M., Tumova, S., Hienola, A., Paveliev, M., Rauvala, H., Saarma, M. (2005) GNDF signalling through Syndecans. ELSO Meeting 2005 (Sep. 3-6, 2005) Poster Abstracts.

Bespalov, Maxim M., et al., "Heparan sulfate proteoglycan syndecan-3 is a novel receptor for GDNF, neurturin and artemin," The Journal of Cell Biology, vol. 192, No. 1, Jan. 3, 2011, pp. 153-169 and S1-S4.

A

B

IP: Syndecan-3

A

GDNF     HB-GAM     Merged

B

A

GDNF-matrix

B

BSA-matrix

C

A

B

A

UNTRSU6656

B

AdGFPAdDN-Src/GFP

RECEPTOR FOR GDNF FAMILY LIGANDS

FIELD OF THE INVENTION

The present invention is generally directed to a novel receptor for GDNF family ligands (GFLs). It provides methods for identifying a molecule, which interferes with the interaction between a glial cell-line derived neurotrophic factor (GDNF) family ligand (GFL) and a heparan sulfate proteoglycan (HSPG) in order to increase the biodistribution of GFLs. The present invention further provides a complex for identifying said molecule. The present invention further provides a method for preventing or delaying a neurodegenerative process as well as a method for prophylactic treatment or treatment of a disorder in the nervous system by administering the molecules of the present invention. The present invention further provides a method for identifying a molecule, which activates heparan sulfate proteoglycan (HSPG) and triggers intracellular signaling of the Src family kinase (SFK) signaling pathway, whereby leading to spread and migration of neuronal cells and neurite outgrowth.

BACKGROUND OF THE INVENTION

Glial cell line-derived neurotrophic factor (GDNF), neurturin (NRTN), artemin (ARTN) and persephin (PSPN) are secreted growth factors collectively known as GDNF family ligands (GFLs) (reviewed by Airaksinen and Saarma, 2002). They play a pivotal role in differentiation and maintenance of the nervous system.

The conventional receptor complex for soluble GFLs consists of a ligand-specific glycosylphosphatidylinositol (GPI)-anchored co-receptor GFRα and a signal-transducing module, the receptor tyrosine kinase RET. GDNF activates either RET or NCAM via GFRα1, NRTN activates via GFRα2, ARTN activates via GFRα3 and PSPN uses GFRα4.

Growth factor signaling is modulated by the extracellular matrix (ECM). The activities of many growth factors are affected by interaction with ECM heparan sulfates (HSs) presented by heparan sulfate proteoglycans (HSPGs). Brain development is remarkably dependent on HSPG functioning. The cell surface HSPGs, called syndecans, act as co-receptors for many growth factors and adhesion molecules. Syndecan-3 associates with growing axons and neural processes and is found in most major neuronal migration routes (Kinnunen et al. 1997). Even if GDNF was originally purified by heparin-affinity chromatography (Lin et al., 1993) and shown to interact with HS (Rickard et al., 2003) and to require HS for signaling through the GFRα1-RET complex (Tanaka et al., 2002; Barnett et al., 2002), the molecular identity of HSPGs which bind GDNF and consequently the interaction of NRTN, ARTN and PSPN with heparin or HSPGs has remained obscure. Growth factors have never been demonstrated to signal via HSPG.

Even if GFLs, particularly GDNF, have shown promising results in treatment of Parkinson's disease (Gill et al., 2003) and amyotrophic lateral sclerosis (ALS) (Henderson et al., 1994), other studies have failed to show strong clinical benefits for GDNF (Lang et al., 2006). Also, even if confusion of heparin with GDNF, NRTN or ARTN into rat striatum affected their biodistribution (Hamilton et al., 2001; US 2002/0114780), the mechanism thereof has remained unstudied. Therefore the object of present invention is to found a reason for the above mentioned failure and by unsettling the reason to enable the development of a remedy useful for treating the increasing number of subjects presenting with disorders in the nervous systems.

SUMMARY OF THE INVENTION

When studying the interaction of immobilized GFLs, including GDNF, NRTN, ARTN and PSPN, with syndecan-3, it was surprisingly found that all said immobilized, matrix-bound GFLs, except persephin (PSPN), use a fundamentally different receptor than soluble GFLs, which bind to the ligand-specific glycosylphosphatidylinositol-anchored co-receptor GFRα and signal through the receptor tyrosine kinase RET. The present inventors found that all immobilized, matrix-bound GFLs, except persephin, activate a novel receptor syndecan-3, a transmembrane heparan sulfate proteoglycan (HSPG), by binding to its heparan sulfate chains with high affinity. For the first time growth factors were demonstrated to signal via HSPG. The present invention is based on this novel and surprising discovery and the characteristic features of the invention are presented in the claims.

The present invention contemplates an in vitro method for identifying a molecule, which interferes with the interaction between a glial cell-line derived neurotrophic factor (GDNF) family ligand (GFL) and a heparan sulfate proteoglycan (HSPG), by screening a library of molecules against a matrix anchored complex comprising at least one immobilized glial cell-line derived neurotrophic factor family ligand (GFL) and at least one heparan sulfate proteoglycan (HSPG), wherein the interfering molecule is isolated based on its capacity to replace a GFL in said anchored complex. In a preferred embodiment the isolated purified anchored complex is present in a neuronal cell. Preferably the anchored complex is attached to a solid support. GFL is preferably GDNF, a neurturin or an artemin molecule. In a preferred method the HSPG is a syndecan-3. In another embodiment HSPG is an oligomerized syndecan-3.

The present invention also provides a complex for identifying a compound, which interferes with the interaction between a GFL and a HSPG, wherein said complex comprises at least one immobilized GFL and at least one heparan sulfate proteoglycan (HSPG) anchored to a matrix. The complex can be used in neuronal tissue or in neuronal cells. As anchored GFL-HSPG complexes GFLs are useful in for identifying molecules which interfere with the interaction between a GFL and a HSPG, preventing the binding of GFLs to HSPG leading to a better biodistribution of the GFLs, GDNF, neurturin and artemin. The anchored complex can be attached to a solid support.

The present invention also provides a method for preventing or delaying a neurodegenerative process, wherein a molecule, which is identified with the method of claim 1 and interferes with the interaction between a glial cell-line derived neurotrophic factor family ligand (GFL) and a HSPG, is administered to a subject in need, in an amount, which is capable of replacing said GFL forming a complex between at least one immobilized GFL and at least one heparan sulfate proteoglycan (HSPG), whereby leading to release of GFL and increased biodistribution of GFL. In a preferred embodiment the neuronal cells are cortical neurons, more preferably embryonic cortical neurons. In another embodiment the matrix anchored complex between immobilized GFL and heparan sulfate proteoglycan (HSPG) comprises syndecan-3 or oligomerized syndecan-3. In one embodiment the neuronal cell is a cortical neuron, more preferably an embryonic cortical neuron. In another embodiment the matrix anchored complex between immobilized GFL and heparan sulfate proteoglycan (HSPG) comprises syndecan-3 or oligomerized syndecan-3.

The present invention also provides a method for prophylactic treatment or treatment of a disorder in the nervous system, wherein a molecule, which is identified with the method of claim 1 and interferes the interaction between a GFL and a HSPG is administered to a subject in need, in an amount, which is capable of replacing the GFL in the complex between at least one immobilized GFL and at least one heparan sulfate proteoglycan (HSPG), whereby leading to release of GFL and increased biodistribution of GFL. In a preferred embodiment the neuronal cells are cortical neurons, more preferably embryonic cortical neurons. In another embodiment the matrix anchored complex between immobilized GFL and heparan sulfate proteoglycan (HSPG) comprises syndecan-3 or oligomerized syndecan-3.

The present method is useful for prophylactic treatment or treatment of a disorder in the nervous system, wherein said disorder of the nervous system is caused by hypoxia, hypoglycemia, central nervous system trauma, intoxication by drugs or gases, administration of chemotherapy, alcohol abuse, or neurodegenerative disease, such as Parkinson's disease, amyotrophic lateral sclerosis (ALS), stroke syndromes, epilepsy, migraine or pain syndromes.

The present invention provides a method for preventing or delaying a neurodegenerative process, comprising administration of a glial cell-line derived neurotrophic factor (GDNF) family ligand (GFL) with or without a HSPG to a neuronal cell in a subject in need, in an amount capable of forming a complex between at least one immobilized GFL and at least one heparan sulfate proteoglycan (HSPG) which is anchored to a matrix and triggers on an intracellular signaling pathway, whereby leading to spread and migration of neuronal cells and neurite outgrowth. In a preferred embodiment, the signaling pathway is Src family kinase (SFK) signaling pathway.

The present invention also provides a method for prophylactic treatment or treatment of a disorder in the nervous system, wherein at least one GFL is administered to a subject in need in an amount, which is capable of triggering an intracellular signaling pathway, whereby leading to spread and migration of neuronal cells and neurite outgrowth. In a preferred embodiment the neuronal cells are cortical neurons, more preferably embryonic cortical neurons. In one embodiment the matrix anchored complex between immobilized GFL and heparan sulfate proteoglycan (HSPG) comprises oligomerized syndecan-3. In one embodiment the signaling pathway is Src family kinase (SFK) signaling pathway.

The present method also provides a method for identifying a molecule, which mimics a glial cell-line derived neurotrophic factor family ligand (GFL) by screening a library of molecules against a matrix anchored complex comprising at least one immobilized glial cell-line derived neurotrophic factor family ligand (GFL) and at least one heparan sulfate proteoglycan (HSPG), wherein the mimicking molecule is isolated based on its capacity to activate heparan sulfate proteoglycan (HSPG) and trigger intracellular signaling of the Src family kinase (SFK) signaling pathway, whereby leading to spread and migration of neuronal cells and neurite outgrowth.

BRIEF DESCRIPTION OF THE FIGURES

FIG. 1 shows GFL binding to heparin.

FIG. 1A depicts elution of $^{125}$I-GFLs from heparin-sepharose column by step NaCl gradient. PSPN elutes at 0.5 M NaCl concentration indicating very weak interaction with heparin. GDNF elutes at 0.75-1 M salt concentration, ARTN at 1-1.5 M salt and NRTN elutes from heparin column at 1.5 M salt.

FIG. 1B depicts that heparin binding to immobilized GFLs was followed by surface plasmon resonance using IAsys optical biosensor. The dissociation constants were determined from dynamics (full figures) as well as equilibrium data (inserts) and their values are indicated in the panels.

FIG. 2 shows that GDNF, NRTN and ARTN bind directly to syndecan-3 with high affinity.

FIG. 2A depicts that syndecan-3 (S3) binding to GFLs, immobilized on the cuvette, was followed by surface plasmon resonance. The dissociation constants were determined from dynamics (full figures) as well as equilibrium data (inserts) and their values are indicated in the panels.

FIG. 2B depicts that GDNF interacts directly with syndecan-3 in rat glioma C6 cell line. Chemical cross-linking of $^{125}$I-GDNF bound to C6 cells was followed by immunoprecipitation with anti-syndecan-3 antibodies in untreated cells (UNTR), cells pretreated with heparinase III (H'ase III) and cells pretreated with PI-PLC. Alternatively, 150-fold molar excess of unlabeled (Cold) GDNF and HB-GAM, or 1 μg/ml heparin were added simultaneously with $^{125}$I-GDNF. In the negative control no syndecan-3 antibodies were added (No AB). High molecular weight band in the upper part of the gel corresponds to GDNF-syndecan-3 complex. Equal loading of the proteins was confirmed by silver staining of the gel (data not shown).

FIG. 3 shows GDNF localization in the extracellular matrix.

FIG. 3A shows immunohistochemical staining of E15 sagittal mouse kidney sections. GDNF is residing primarily in the ECM. GDNF staining pattern largely overlaps with ECM molecule HB-GAM.

FIG. 3B shows Western blotting of proteins extracted from dissociated P9 mouse brain and kidney tissues. Lysates from ECM and membrane-associated fractions were separated by SDS-PAGE and Western blots were stained with anti-GDNF (upper panel) or anti-HB-GAM antibodies (lower panel). 16 kD and 17 kD bands correspond to GDNF and HB-GAM, respectively.

FIG. 4 shows that GDNF, NRTN and ARTN induce SHEP cell adherence and SFK activation in HSPG-dependent manner.

FIG. 4A shows RT-PCR with syndecan-3 specific primers of the cDNA from SHEP cells. The resulting 140 bp band represents syndecan-3 mRNA-derived PCR product (lane 2). Lane 1: molecular weight markers with the size in base pairs (bp) are indicated on the left.

FIG. 4B shows crystal violet staining of SHEP cells plated on immobilized GDNF, ARTN, NRTN and PSPN with (H'aseIII) or without (UNTR) Heparinase III pretreatment.

FIG. 4C demonstrates the quantification of SHEP cell adherence to immobilized ΔN-GDNF compared to GDNF. Cells were plated on GDNF untreated (UNTR), or they were pretreated with PI-PLC, Chondroitinase ABC (Ch'ase ABC), NCAM function-blocking antibodies (NCAM BLK) or GDNF function-blocking antibodies (GDNF BLK). Error bars show standard error of means (SEM) from three independent assays.

FIG. 4D demonstrates quantification of attached SHEP cells on immobilized GFL. Some cells were treated with heparinase III. Quantification also includes controls with cell attachment on BSA and attachment of cells treated with heparinase III on tissue culture plate. Error bars show SEM from three independent assays.

FIG. 4E shows a Western blot for activated Src family kinase detection in lysates from SHEP cells plated on GDNF, ΔN-GDNF or BSA. In control experiments cells plated on GDNF were treated with heparinase III (HIII) or PI-PLC. Western blots were stained with anti-pY$^{418}$Src (upper panel) or anti-Src (lower panel) antibodies.

FIG. 5A shows neurite outgrowth in E17 rat hippocampal neurons (stained with tubulin-βIII antibodies) on immobilized GDNF.

FIG. 5B shows neurite outgrowth in the same neurons plated on BSA.

Figure 5:
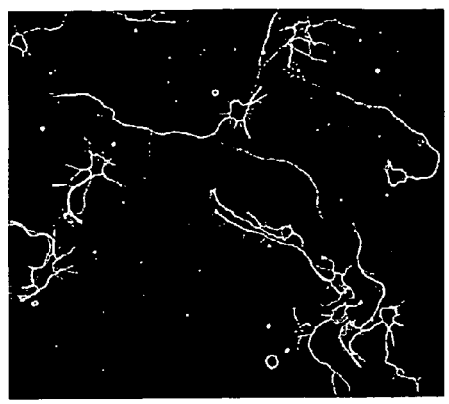
FIG. 5 shows that immobilized GDNF induces neurite outgrowth in rat embryonic hippocampal neurons.
Figure 5:
Figure 5:
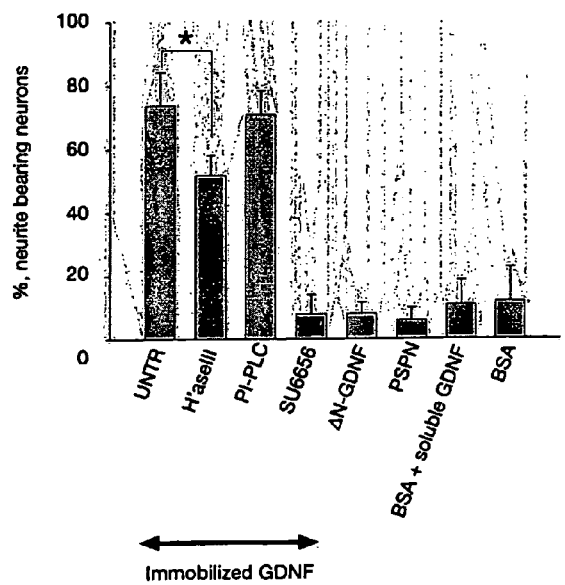

FIG. 5C shows quantification of neurite outgrowth on immobilized GDNF, ΔN-GDNF, PSPN and BSA. Neurons plated on GDNF were untreated (UNTR), preincubated with heparinase III (H'aseIII), PI-PLC or SFK inhibitor SU6656. As a control, soluble GDNF was added to neurons grown on BSA. Error bars show SEM from three to five independent experiments (asterisk corresponds to p<0.05).

Figure 6:
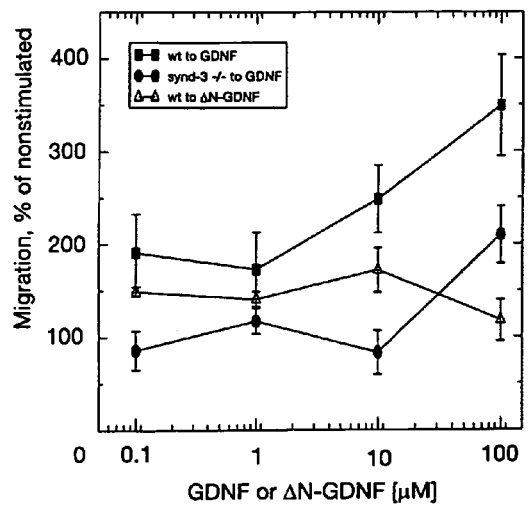
Figure 6:
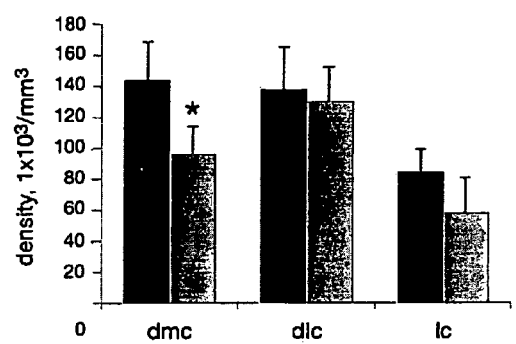
Figure 6:
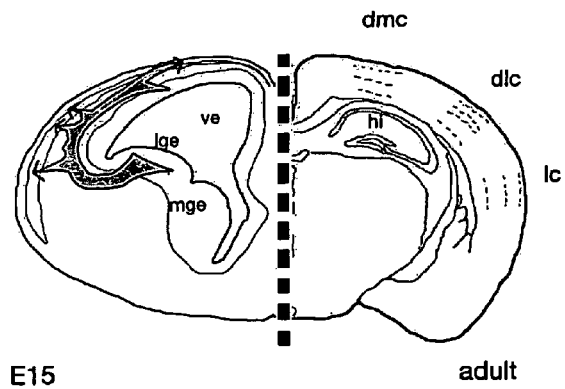

FIG. 6 shows that GDNF stimulates migration of embryonic mouse cortical neurons via syndecan-3.

FIG. 6A depicts E15 cortical neurons in modified Boyden chamber migration assay migrate towards wtGDNF (closed squares) but not towards ΔN-GDNF (open triangles). Cortical neurons from syndecan-3-deficient mice (black circles) migrate towards GDNF less efficiently than wild type neurons. Error bars show SEM from three independent experiments.

FIG. 6B depicts that syndecan-3-deficient mice have less GABAergic neurons in cerebral cortex. The cell density is almost identical to wild type in the most lateral parts of the cortex, while in syndecan-3 knockouts the GABAergic density is significantly smaller in the most dorsal parts of the cortex. Dorso medial cortex (dmc), dorso lateral cortex (dlc), lateral cortex (lc). Error bars show SEM (asterisk corresponds to p<0.05).

FIG. 6C is a schematic presentation shows the cortical areas, where the density measurements were made. Arrow shows the tangential migration route in E15 mice. Lateral ganglionic eminence (lge), medial ganglionic eminence (mge), ventricle (ve), hippocampus (hi).

Figure 7:
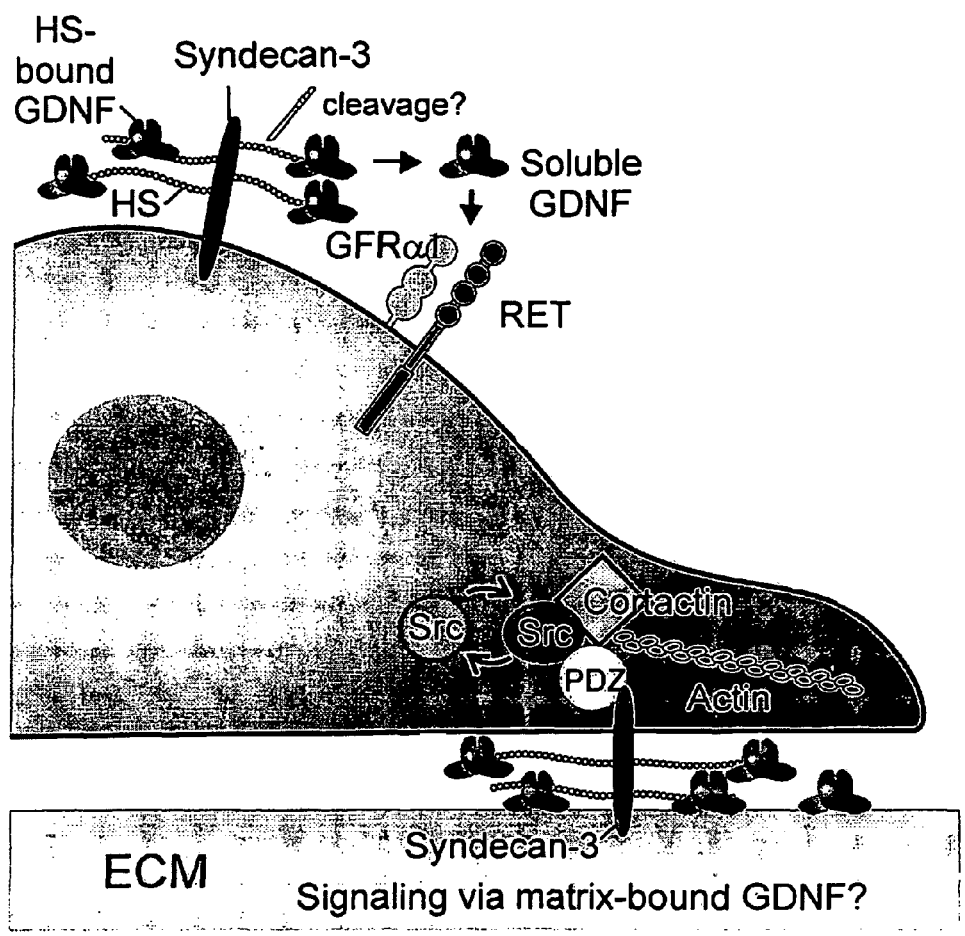

FIG. 7 is a hypothetical model of GDNF signaling mediated by syndecan-3. Matrix-bound GDNF may directly induce syndecan-3 signaling via interaction with heparan sulfate (HS) chains of the receptor. Alternatively, syndecan-3 can modulate diffusible GDNF induced RET (or NCAM) signaling.

Figure 8:
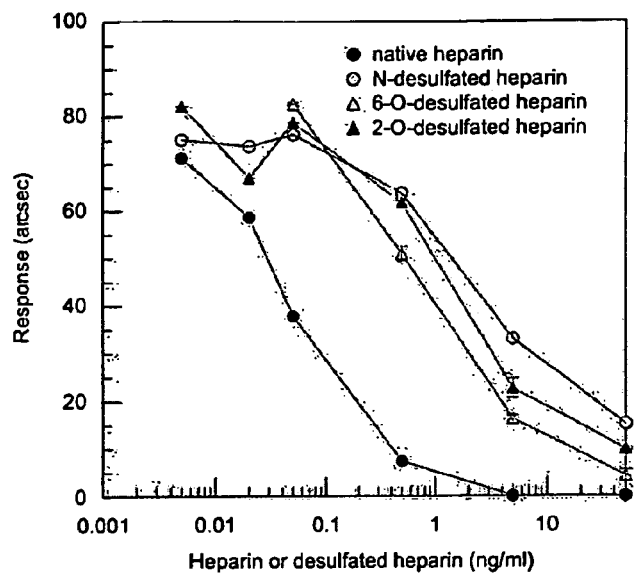
Figure 8:
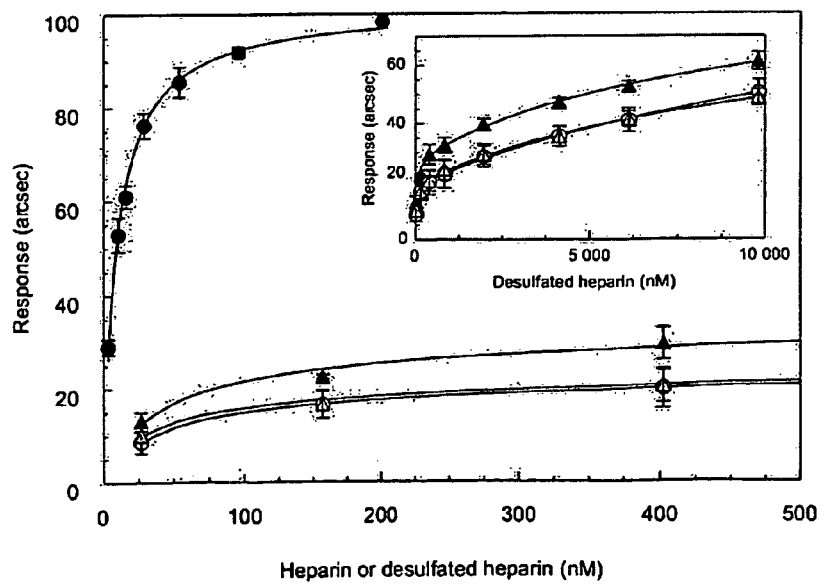

FIG. 8 depicts the interaction of GFLs with desulfated heparins.

FIG. 8A. GDNF binding to heparin-BSA cuvette using the IAsys optical biosensor: competition by heparin and desulfated heparins. Corresponding IC50 values are presented in Table 1.

FIG. 8B. Direct interaction between immobilized GDNF and desulfated heparins or nascent heparin was analyzed by SPR using the IAsys optical biosensor. Analysis by equilibrium titration demonstrated significant decrease in affinity for all types of desulfated heparin when compared to native heparin binding to GDNF. Data were fitted as described in the methods section and the dissociation constants are presented in Table 1. The symbols are as described in FIG. 8A.

Figure 9:
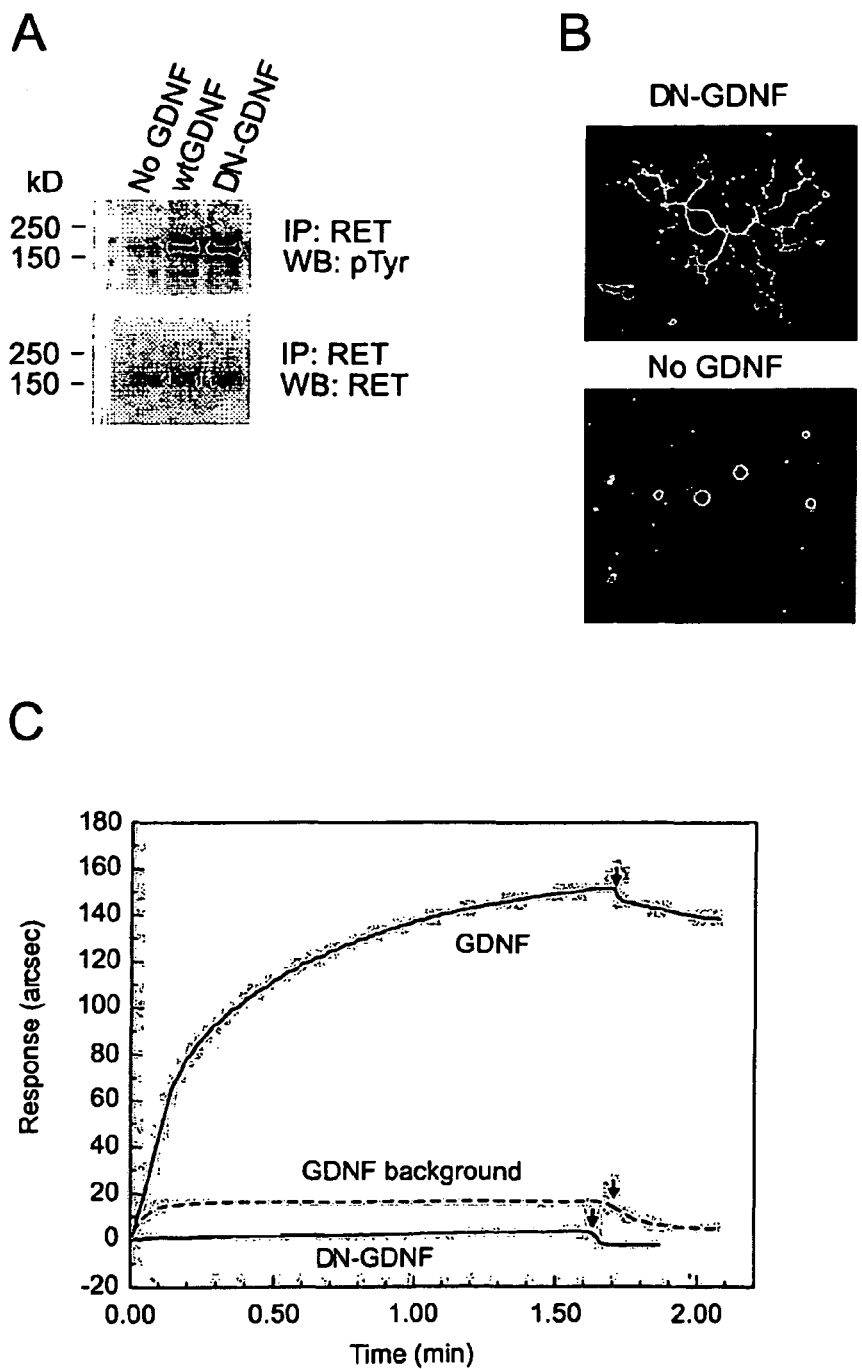

FIG. 9 depicts the characterization of ΔN-GDNF variant.

FIG. 9A. Soluble heparin-binding deficient GDNF mutant (ΔN-GDNF) activates RET phosphorylation as well as wild type GDNF. Lysates of untreated (No GDNF) Neuro2a cells or Neuro2a cells incubated with 100 ng/ml of GDNF (wt-GDNF) or with 100 ng/ml of ΔN-GDNF were immunoprecipitated (IP) with antibodies to RET and the Western blots (WB) were reacted with antibodies to phosphotyrosine (pTyr; upper gel) and antibodies to RET (lower gel).

FIG. 9B. Soluble ΔN-GDNF at 100 ng/ml induces neurite outgrowth from P30 DRG neurons (upper panel), whereas there are no detectable neurites in the absence of GDNF (lower panel).

FIG. 9C. Unlike wtGDNF, ΔN-GDNF fails to bind heparin. Real-time binding of wtGDNF and ΔN-GDNF to immobilized heparin was followed by surface plasmon resonance. The first part of the curve represents the association phase. Arrows indicate the beginning of the dissociation phase.

Figure 10:
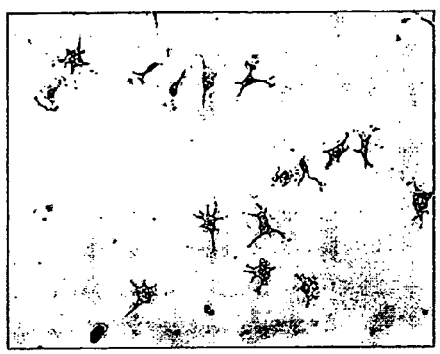
Figure 10:
Figure 10:
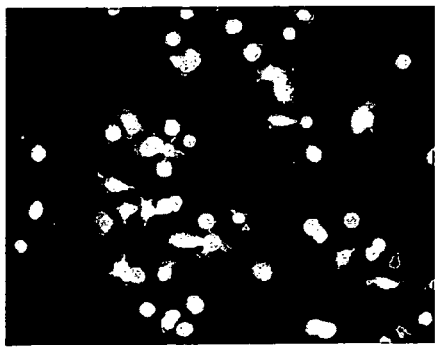
Figure 10:
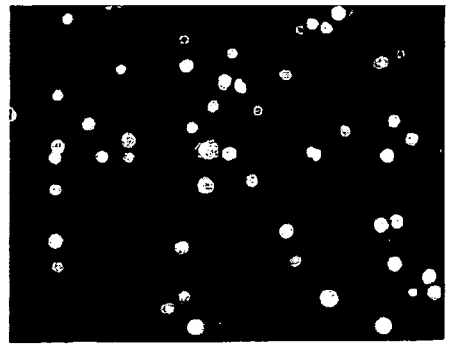

FIG. 10 depicts SHEP cells spreading depends on SFK activity.

FIG. 10A. SHEP cell adherence and spreading on immobilized GDNF in the absence (UNTR) or presence of SFK inhibitor SU6656. Cell spreading on immobilized GDNF was impaired in the presence of the inhibitor whereas adherence of SHEP cells was not significantly affected by SU6656.

FIG. 10B. Adherence and spreading of SHEP cells infected with adenovirus expressing GFP (AdGFP) or dominant-negative Src (AdDN-Src/GFP) on immobilized GDNF. Infection of cells with AdDN-Src/GFP resulted in SHEP spreading failure to spread on immobilized GDNF. GFP-expressing adenovirus (AdGFP) did not affect SHEP cell spreading on GDNF-matrix.

Figure 11:
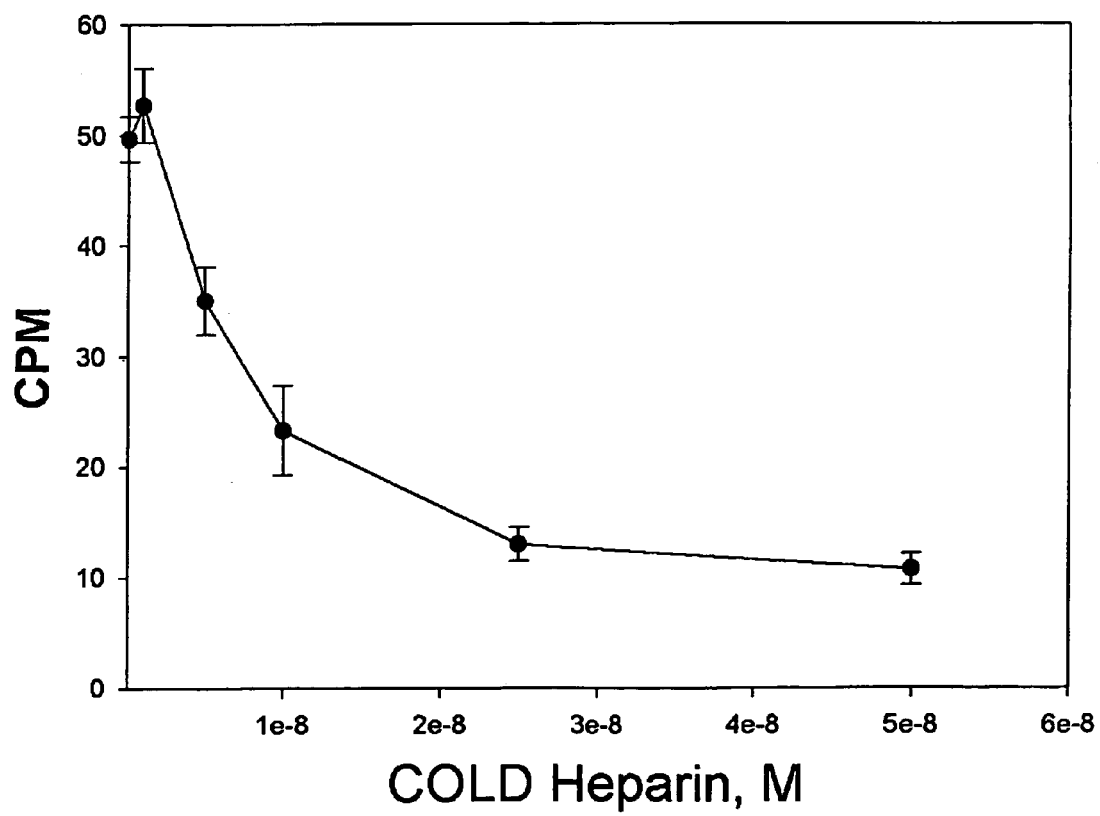

FIG. 11 depicts displacement of $^3$H-heparin with cold heparin. The scintillation proximity assay (SPA) technology (Amersham) was used to assay the ability of the low molecular weight molecule to displace tritium labeled heparin from GDNF.

DETAILED DESCRIPTION OF THE INVENTION

GDNF family ligands (GFLs) comprise GDNF (glial cell line-derived neurotrophic factor), NRTN (neurturin), ARTN (artemin) and PSPN (persephin).

The present invention is the first demonstration that the interaction of matrix-bound GFLs and HSPG syndecan-3 can activate signal transduction through heparin sulfate proteoglycan. Thus HSPG syndecan-3 is a novel receptor for GDNF, NRTN and ARTN. Signaling through syndecan-3 is important for hippocampal neurite outgrowth and brain cortex formation. This knowledge is a breakthrough in successful therapeutic use of GFLs by promoting the generation of effective GFL mimetics.

GDNF has been used for the treatment of Parkinson's disease patients with variable success. The negligible benefit of GDNF in the recent clinical trials of Parkinson's disease by Amgen Inc. (Lang et al. 2006) may result from limited tissue distribution due to ECM trapping. In the present invention syndecan-3 has been identified as a factor, which may compromise distribution of GDNF, NRTN and ARTN when they are applied into the brain. GFLs can be applied into the brain by direct injection for example using a device containing cells expressing GFLs. The present invention promotes identification and synthesis of GFL variants (e.g. ΔN-GDNF that was used in the present invention) that efficiently activate RET but lack the heparin-binding sites and do not interact with HSPGs in extracellular matrix. With such improved GFLs the treatment of Parkinson's disease and ALS can be more efficient than currently.

Immobilized matrix-bound GFLs, except persephin, were found to activate syndecan-3, a transmembrane heparan sulfate proteoglycan, by binding to its heparan sulfate chains with high affinity. Syndecan-3 mediates both cell spreading and neurite outgrowth on the GFL-matrix via Src kinase activation. Moreover, GDNF promotes migration of cortical neurons in a syndecan-3-dependent manner and thus can play a central role in cortical development. It was demonstrated that mice lacking syndecan-3 or GDNF show a reduced number of cortical GABAergic neurons.

Administration by coinfusion of heparin with GFLs increased the biodistribution of GFLs with the exception of persephin. The reason for this increased biodistribution is the surprising finding that heparin prevented GFL binding locally to syndecan-3 or HSPG in the brain ECM. Thus, the present invention provides a method, which is useful as therapeutic use of GFLs by promoting the generation of effective GFL variants, lacking affinity to HSPGs and thus with increased biodistribution.

GDNF, NRTN and ARTN Interact with Heparin and HSPG Syndecan-3

In one embodiment the invention discloses in vitro methods for binding of GDNF, ARTN and NRTN to heparin. GDNF, ARTN and NRTN bind to heparin with $K_d$s in the range of 10-50 nM. More significantly, heparin-binding GFLs also bind the HSPG syndecan-3 with similar affinity, suggesting that syndecan-3 could be their natural binding partner in the developing brain.

GDNF, NRTN and ARTN Act Via Syndecan-3 and Trigger SFK Signaling

Figure 2:
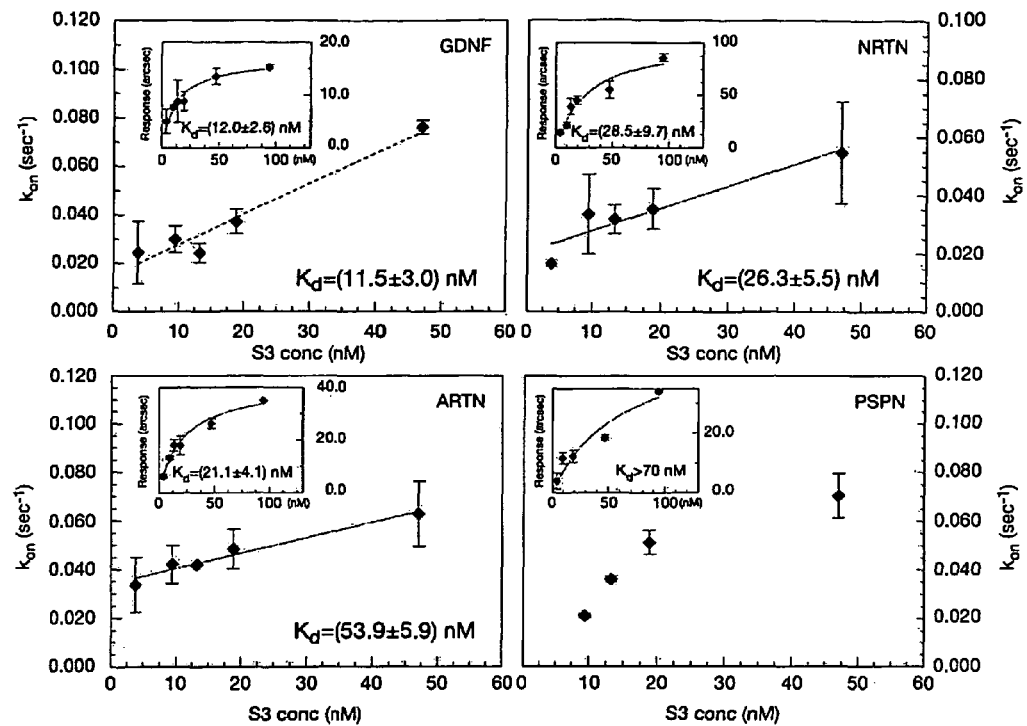
Figure 2:
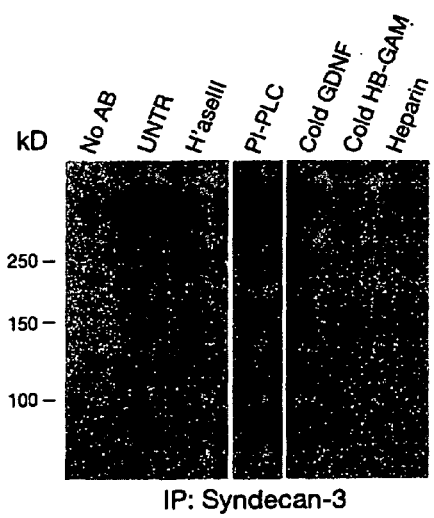

The present inventors show that immobilized GDNF, NRTN and ARTN can stimulate cell adhesion and spreading via syndecan-3 without involvement of their conventional receptors. It was shown that binding of GDNF to the HS chains of syndecan-3 triggers SFK signaling and that the SFK activity is required for cell spreading, but not for initial attachment. Based on these findings the interaction between immobilized GFLs and syndecan-3 first leads to the receptor anchoring to the GFL-matrix, and then subsequent signaling activates SFK leading to full spreading. The intermediate step can involve syndecan-3 oligomerization triggered by GFL binding. Syndecan-3 cytoplasmic domain is thought to be associated directly or via adaptor proteins with SFK. Oligomerized syndecan-3 thus may locally increase SFK concentration leading to transphosphorylation of SFK. Contribution of CASK kinases may also be important for the SFK activation. GDNF, NRTN and ARTN all have at least one putative heparin-binding site. In particular, the primary heparan sulfate/heparin binding site is at the N-terminus of GDNF (FIG. 9). Since all GFLs are produced as covalently linked homodimers, they contain two heparin-binding sites capable of binding two syndecan-3 molecules. As syndecan-3 bears several HS chains, its interaction with GFLs most likely leads to oligomerization. Indeed, the high molecular weight complex of GDNF and syndecan-3 detected after chemical cross-linking in C6 glioma cells could correspond to syndecan-3 oligomers (FIG. 2B).

Interestingly, because syndecan-3 has several HS chains, one molecule of syndecan-3 can simultaneously bind multiple GFL homodimers. Thus, compared with the GFRα/RET receptor complex, which binds GFL with only one GFL homodimer syndecan-3 is a high-affinity/high-capacity receptor for GFLs.

The present inventors show that GDNF is localized predominantly in the ECM and cell membrane. GFLs are secretory proteins that have the PrePro sequence that targets them to secretory vesicles. The PrePro sequence is cleaved by proteases upon arrival of the proteins to trans-Golgi network by proteases like furin. Heparan sulfates that are abundant in the ECM and on the outer leaflet of the plasma membrane sequester GDNF, NRTN and ARTN in the extracellular space. Interaction with matrix HSPGs can dramatically change the properties and distribution of the heparin binding GFLs.

GFLs Variants Lacking Affinity to HSPG

The present inventors demonstrate that coinfusion of heparin with GDNF, NRTN or ARTN into rat striatum markedly increased their biodistribution, because the heparin prevented GFL binding locally to syndecan-3 or HSPGs in the brain ECM. This knowledge enables the development of therapeutic use of GFLs by promoting the generation of effective GFL variants, lacking affinity to HSPGs and thus with increased biodistribution.

Immobilized GDNF Induce Robust Neurite Outgrowth in Embryonic Hippocampal Neurons Via Cell Surface HSPGs and SFK Activation The present invention shows that immobilized, but not soluble GDNF, induce robust neurite outgrowth in embryonic hippocampal neurons via cell surface HSPGs and SFK activation. No evidence for involvement of other GFL receptors was found. Rat embryonic hippocampal neurons express negligible levels of RET and neither release of GPI-anchored GFRα1 by PI-PLC nor NCAM-blocking antibodies had any effect on the GDNF-induced neurite outgrowth. This is in contrast to data of Paratcha et al. (2003) who found that NCAM-blocking antibodies reduced GDNF-induced neurite outgrowth in hippocampal neurons. The earlier work measured the length of neurites initiated by GDNF whereas our assay analyzed the number of neurons bearing neurites. Therefore, we actually studied the initiation of neurite outgrowth rather than the progression of already formed neurites.

Our in vitro data indicates that GDNF binding to syndecan-3 activates SFK by inducing cell spreading and neurite outgrowth in RET-negative neurons. The migration of embryonic cortical neurons was shown to be dependent on GDNF, even if no measurable levels of RET or NCAM (Pozas and Ibáñez, 2005) were demonstrated. Thus, syndecan-3 can be used as GDNF receptor in these neurons.

During cerebral cortex formation, inhibitory GABAergic interneurons originate mainly from the medial ganglionic eminence (MGE) and then migrate tangentially into the developing cortical layers (FIG. 6C).

Syndecan-3 Mediates GDNF-Induced Migration of Cortical Neurons

The present inventors demonstrate that syndecan-3 mediates GDNF-induced migration of cortical neurons. In the migration assay, embryonic cortical neurons were efficiently stimulated to migrate by GDNF. Conversely, the heparin-binding-deficient ΔN-GDNF mutant failed to induce migration and this effect was also abolished in neurons lacking syndecan-3. A specific role of syndecan-3 in the signaling pathway is supported by the fact that syndecan-3 deficient cortical neurons were still capable of migration toward laminin. Additionally, either the differentiation or migration of GABAergic neurons appears to be defective in the syndecan-3 knockout mice, as we can detect a clear drop in the density of these cells in the dorsal cerebral cortex of the syndecan-3-deficient mice. This was done by counting GABAergic neurons stained with anti-GABA antibody.

Syndecan-3 is a New Receptor for Immobilized GDNF, NRTN and ARTN

Consequently, this work identifies syndecan-3 as a new receptor for immobilized GDNF, NRTN and ARTN, fundamentally different from the diffusible GFL-GFRα/RET system. In addition, GFL signaling via syndecan-3 and via GFRα/RET or GFRα/NCAM induce distinct biological effects. Our results clearly show that binding of immobilized GDNF to syndecan-3 alone can induce intracellular signaling leading to the activation of SFKs, and the triggering of cell spreading, neurite outgrowth and migration of embryonic cortical neurons. Moreover, GDNF signaling through syndecan-3 is important for brain cortex formation. Our model (FIG. 7) also supports the idea that the interaction of GDNF, NRTN and ARTN with HS can concentrate GFLs in the vicinity of its conventional receptors GFRα/RET. The model also predicts a new regulatory step in GFL signaling: cleavage of HS or the syndecan-3 ectodomain to regulate the release of diffusible GFLs required for GFRα/RET receptor activation. As such, we suggest that the long-range (chemotactic) signals exerted by diffusible GFLs are mediated by GFRα/RET, whereas the short-range effects are transduced via syndecan-3. This is the first demonstration that a growth factor can activate signal transduction through heparan sulfate proteoglycan, and that the same signaling molecule, GDNF, elicits different biological effects via different receptors when immobilized or as free diffusible protein (FIG. 7).

In one embodiment, the invention contemplates a method for identifying a molecule, which interferes with the interaction between a glial cell-line derived neurotrophic factor (GDNF) family ligand (GFL) and HSPG, by screening a library of molecules against a matrix anchored complex comprising at least one immobilized GFL and at least one heparan sulfate proteoglycan (HSPG), wherein the interfering molecule is isolated based on its capacity to replace the GFL in said anchored complex.

The method of the present invention includes method for identifying a molecule, which mimics a GFL. This method generally involves screening a library of molecules against a matrix anchored complex comprising at least one immobilized GFL and at least one heparan sulfate proteoglycan (HSPG), wherein the mimicking molecule is isolated based on its capacity to interfere with the matrix anchored complex by activating heparan sulfate proteoglycan (HSPG) and trigger intracellular signaling pathway, preferably Src family kinase (SFK) signaling pathway.

The methods are amenable to automated, cost-effective high throughput screening of chemical libraries for lead compounds. Identified reagents find use in the pharmaceutical industries. The reagents may be derivatized and rescreened in vitro and in vivo assays to optimize activity and minimize toxicity for pharmaceutical development.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive) (e.g., Zuckermann, R. N. et al.); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds.

In another aspect, the invention provides a complex for identifying a compound, which interferes the interaction between a GFL and HSPG, wherein said complex comprises at least one immobilized GFL and at least one heparan sulfate proteoglycan (HSPG) anchored to a matrix.
Methods for Therapeutic Use of GFLs The various GFL compounds are also useful in a variety of therapeutic applications as described herein.

The therapeutic use of GFLs promotes the generation of effective GFL mimetics. GDNF has been used for the treatment of Parkinson's disease patients with variable success. The present invention identifies syndecan-3 as a factor, which may compromise distribution of GDNF, NRTN and ARTN when they are applied into the brain. Improved GFL variants (e.g. ΔN-GDNF that was used in this study) that efficiently activate RET but lack the heparin-binding sites and do not interact with HSPGs in extracellular matrix are useful for the treatment of Parkinson's disease and amyotrophic lateral sclerosis (ALS) providing more efficient treatment than currently.

GFLs are useful for development of drugs and therapeutic methods for treatment of several diseases, particularly neuronal diseases. For the GDNF-heparin action and GDNF-syndecan-3 signaling the neuronal diseases can be listed: Parkinson's disease, amyotrophic lateral sclerosis (ALS), morphine and cocaine addiction, regeneration of spinal cord injury. For the NRTN and heparin and NRTN-syndecan 3 signaling the following diseases can be listed: Parkinson's disease, regeneration of spinal cord injury, treatment of brain ischemia and epilepsy. For the ARTN and heparin and ARTN-syndecan-3 signaling the following diseases can be listed: treatment of chronic pain and regeneration of spinal cord injury.

The present therapeutic methods are useful in treating disorders in the nervous system associated with physical or surgical trauma, infarction, toxin exposure, degenerative disease, malignant disease that affects peripheral or central neurons, or in surgical or transplantation methods in which neuronal cells from brain, spinal cord or dorsal root ganglia are exposed to reduced levels of growth factors and require cell death preventive therapy. Such diseases further include but are not limited to CNS lesions, gliosis, Parkinson's disease, Alzheimer's disease, neuronal degeneration, enteric diseases, kidney disease, immunological diseases, diseases of chromaffin cells and the like.

Especially the method can be used to treat neurological diseases such as Parkinson's disease, amyotrophic lateral sclerosis (ALS), drug addiction, alcoholism, stroke syndromes, epilepsy, pain, and disorders of the nervous system.

Thus the invention provides a method of preventing or delaying a neurodegenerative process in a subject, or in selected tissues thereof, comprising administering to the subject or the tissue a physiologically tolerable composition containing a therapeutically effective amount of an agent of the present invention.

For administration, a variety of techniques are available. GFL may be administered by direct brain injection or infusion, topical, intratracheal/nasal administration e.g. through aerosol, intraocularly or within/on implants. Administration is done by intraputamenal administration, which requires brain surgery.

GFLs can be applied into the brain by direct injection for example using a biodelivery device based on encapsulated cell biodelivery technology such as ECB-AD biodelivery product (NsGene A/S, Denmark). The GFLs are administered in the putamen using the EC biodelivery system consisting of an implantable catheter-like device containing modified cells enclosed behind a semi-permeable membrane, which forms a physical and immunological barrier between the host brain and the modified cells expressing GFLs.

If protein is used for administration, generally the amount administered will be empirically determined, typically in the range of about 1 to 30 μg of GFL/day, e.g. 15 or 30 μg of GFL/putamen/day (Slevin et al., 2005). Putamen is a brain area, where neurites from substantia nigra protrude.

Other additives may be included, such as stabilizers, bactericides, etc. which will be present in conventional pharmaceutically acceptable amounts.

If GFL variants are expressed as proteins and delivered exogenously then depending on the expression system they are glycosylated or not. Expression in eukaryotes leads to glycosylated GFL, whereas the expression in *E. coli* provides no sugars. GFL can also be delivered in different viral vectors or by engineered cells and in this case they are likely to be glycosylated. If mutant GFL are used, they will have point mutations (of certain basic amino acids) and deletions (like the GDNF mutant used in the present invention, ΔN-GDNF) to avoid binding to HS but still potent activators of RET.

The compound which mimics GFL is intended to encompass a variety of agents including molecules which include, but are not limited to, peptides, peptidomimetics (e.g. peptoids), amino acids, amino acid analogs, polynucleotides, polynucleotide analogs, nucleotides, nucleotide analogs, organic or inorganic compounds (e.g. including hetero-organic or inorganic compounds), small molecules and drug-like molecules.

Therapeutic compositions of the present invention may include a physiologically tolerable carrier together with the compound of this invention. Any of a variety of mammalian cells or neuronal cells can be treated by the method of the present invention. Also non-mammalian cells, such as Drosophila cells express HSPGs.

The invention will be described in more detail in the following examples, which are provided by way of illustration and should not be construed as restrictive.

Example 1

Cell Cultures and Reagents

Rat glioma C6 cell line and mouse neuroblastoma cell line Neuro2a were from ATCC. Early passage RET-deficient human SHEP cells were provided by Dr. Marc Billaud (CNRS, Lyon, France). MG87-RET cells were provided by Dr. Carlos F. Ibáñez (Karolinska Institute, Stockholm, Sweden). Rat hippocampal neurons were isolated from E17 embryos. Mouse cortical neurons were isolated from E15 embryos. Low molecular weight heparin, heparin-BSA, EDAC/NHS crosslinker, lactoperoxidase, PI-PLC, chondroitinase ABC, globulin-free BSA and cell culture tested BSA were purchased from Sigma. SU6656 was bought from Calbiochem. Heparinase III was from Seikagaku Corp. (Seikagaku's trademark for this product is heparitinase I). The dominant-negative Src adenoviral construct was a kind gift of Dr. David Kaplan (Hospital of Sick Child, Toronto, Canada). Desulfated heparins were kindly provided by Dr. Ryo Takano (Okinawa National College of Technology, Nago, Okinawa, Japan).

Example 2

GFL Iodination and Binding to Heparin-Sepharose

GFL iodination was performed as described (Lindahl et al., 2001). Heparin-sepharose column (Amersham Biosciences) chromatography was performed to assess GFL binding to heparin. GDNF, ARTN, NRTN and PSPN were purchased from PeproTech, Ltd. or R&D Systems, Inc. GFLs were enzymatically labeled with carrier-free [$^{125}$I]NaI (Amersham Biosciences) by the lactoperoxidase method to a specific activity of 100000-200000 cpm/ng as described elsewhere (Lindahl et al., 2001). 15000-20000 cpm of iodinated GFLs, together with 10 μg of the same unlabeled protein as a carrier, were injected into a 1 ml heparin-sepharose column (Amersham Biosciences) in phosphate buffer pH 7.2 containing 100 mM NaCl and 10 mg/ml of BSA. After washing with 5 volumes of the same buffer, iodinated GFLs were eluted from the column by step elution (2 ml) with increasing NaCl concentration. The resulting fractions were counted on Rackbeta 1214 (LKB/Wallac) scintillation counter.

Example 3

Surface Plasmon Resonance (SPR) Studies

The affinities of GFLs for heparin and heparin-like molecules (e.g. syndecan-3) were determined by plasmon surface resonance using the IAsys system (Affinity Sensors, Cambridge, UK). Planar aminosilane cuvettes (Affinity Sensors) were used for protein coupling to avoid problems with mass transport, which occur frequently with matrix surfaces. In the initial approach, heparin-BSA was immobilized to the cuvette surface using the manufacturer's instructions and different ligand concentrations were used to determine association ($k_a$) and dissociation ($k_{dis}$) rates using the IAsys Fastfit software. The dissociation constant $K_d$ was determined from the binding dynamics as $K_d = k_a/k_{dis}$, or from equilibrium response (R) using a simple Langmuir fit: $R=(R_{max}*C)/(K_d+C)$, where C is the ligand concentration. Because all ligands except PSPN displayed background binding to a control BSA cuvette, $K_d$s were also determined in a system where GDNF, ARTN, NRTN and PSPN were immobilized to the aminosilane surface and different concentrations of heparin were presented in a solution. The dissociation constants were determined from binding dynamics and equilibrium response. The same cuvettes were used to test binding of heparan sulfate proteoglycan syndecan-3, which was purified as an ectodomain from early postnatal rat brains by HB-GAM affinity chromatography (Raulo et al., 1994).

Specifically desulfated heparins (Takano et al., 1998) were used to assess the involvement of different sulfate groups in the GDNF-heparin interaction by following direct binding to GDNF cuvette, or by competing out GDNF binding to the heparin-BSA cuvette. Dissociation constants were determined from direct binding using increasing GDNF concentrations and by fitting the data to $R=(R_{max}*C)/(K_d+C)$ for heparin. For desulfated heparins, the best fit was achieved using equation $R=(R_{max1}*C)/(K_{d1}+C)+(R_{max2}*C)/(K_{d2}+C)$, where $K_{d1}$ and $K_{d2}$ are apparent dissociation constants derived for two heparin sites of different affinities with maximum equilibrium response $R_{max1}$ and $R_{max2}$, respectively.

GDNF, NRTN and ARTN Interact with Heparin and HSPG Syndecan-3

Figure 1:
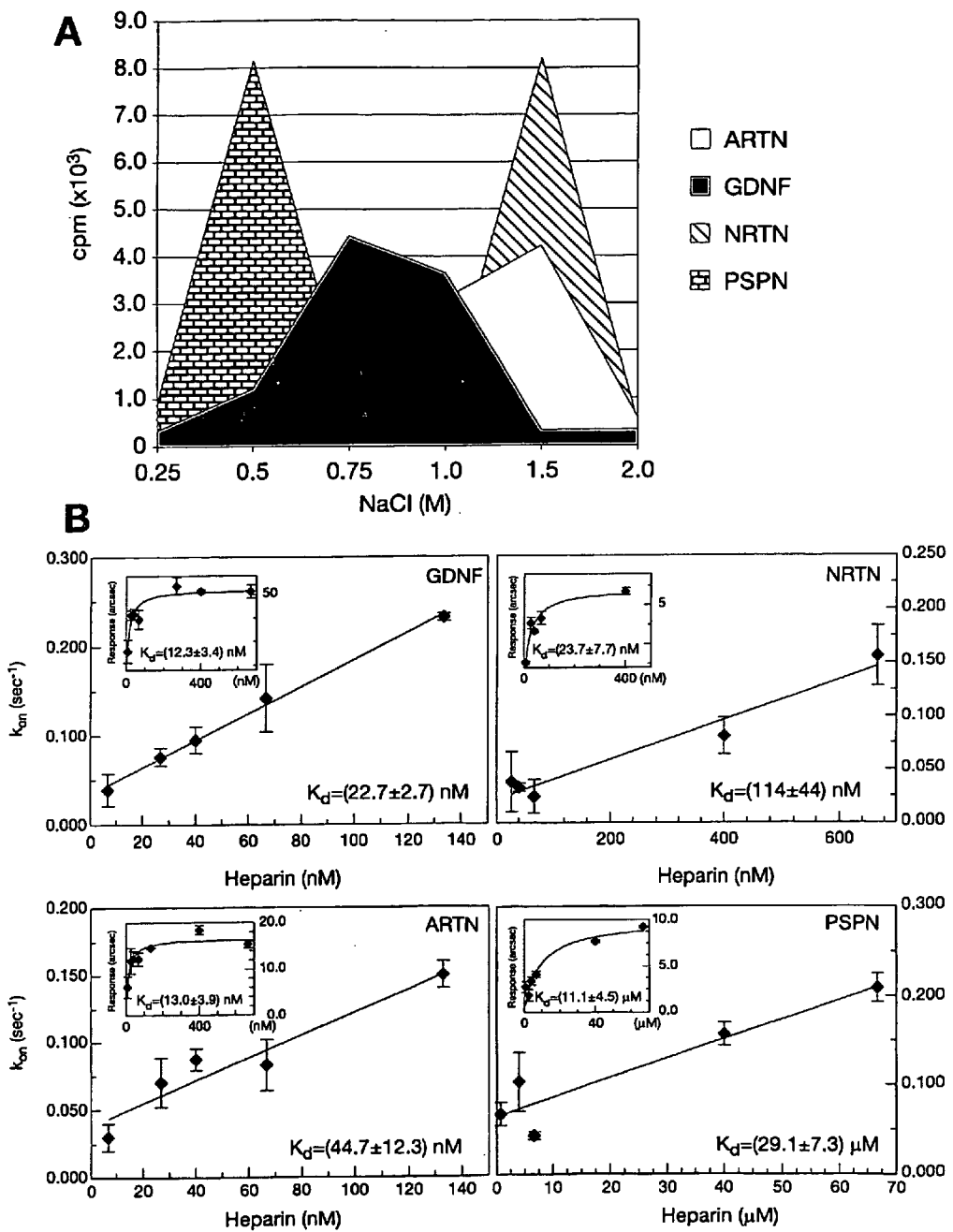

It was first studied whether all GFLs bind heparin and what structural determinants of heparin are required for this interaction. We tested the presence of putative heparin binding sites, which according to Cardin and Weintraub, 1989 are present in the primary structure of GDNF, NRTN and ARTN, but not in PSPN by testing the binding of $^{125}$I-labeled GFLs to heparin-sepharose column (FIG. 1A). GDNF, NRTN and ARTN bind strongly to heparin, whereas PSPN does not.

The affinity of GFLs for heparin and HS was measured by SPR (surface plasmon resonance), implementing dynamics and equilibrium response. The dissociation constants for GDNF, NRTN and ARTN were all between 10-50 nM, with the exception of dynamics-derived $K_d$ for NRTN, which was more than 100 nM. PSPN had three orders of magnitude lower affinity for heparin than the other ligands; the $K_d$ was 29.1 μM (dynamics) or 11.1 μM (equilibrium) (Table 1 and FIG. 1B). The affinity of $^3$H-labeled heparin for GDNF was tested using a third independent method, scintillation proximity assay (Leppänen et al., 2004), and the $K_d$ obtained was very similar that resulted in very similar $K_d$ value (~10 nM; data not shown).

Structural determinants of heparin-GDNF interaction were studied by SPR using different heparin modifications in the heparin competition assay, and by direct binding to immobilized GDNF. GDNF bound all the desulfated heparins much more weakly ($K_d$ of 9.5 μM, 18 μM and 11.4 μM for 2-O-, 6-O- and N-desulfated heparin, respectively) than native heparin ($K_d$ of 9.5 nM), indicating that all tested sulfate groups of heparin were important for the interaction (FIG. 8 and Table 4). To test whether heparin-binding GFLs would bind to natural HSPGs we used SPR to assay the direct interaction between immobilized GFLs and the extracellular domain of syndecan-3 purified from rat brain (Raulo et al., 1994), which carries natural HS side chains. The dissociation constants for GDNF, NRTN and ARTN were in the 10-50 nM range (FIG. 2A), indicating high affinity binding for syndecan-3 and supporting the notion that these GFLs could directly interact with HSPGs at the cell surface and/or in the ECM. The binding occurs specifically via HS chains, since heparinase III treatment strongly inhibited the interaction of GDNF and syndecan-3 (FIG. 2B). For PSPN, dynamics data could not be fit with a simple curve and because of limiting concentrations of syndecan-3, $K_d$ was only estimated to be more than 70 nM. Thus it appears that PSPN binds syndecan-3 with much lower affinity than the rest of the GDNF family ligands (FIG. 2A).

Example 4

RT-PCR

RNA from SHEP cells was isolated using RNAwiz (Ambion). First strands were built with random primers using Superscript II (Invitrogen). 35 cycles of PCR were performed with ATG GCC ATT GCT TAC CTG G (SEQ ID NO: 1) as a forward primer and AAG CGC ATG GCT GTC TCA A (SEQ ID NO: 2) as a reverse primer. Dynazyme II (Finnzymes) polymerase was used and the annealing temperature was 58° C.

Example 5

Chemical Cross-Linking and Immunoprecipitation

Glioma C6 cells were plated on 6-well plates and grown to 70% confluency. Cells were incubated with 1 nM $^{125}$I-GDNF for 2 hours in binding buffer (Dulbecco's modified Eagle's medium, 0.2% BSA and 15 mM Hepes, pH 7.2) on ice. Unbound ligand was removed by washing three times with ice-cold PBS. The chemical cross-linker ethyl-dimethyl-aminopropyl-carbodimide (EDAC) supplemented with N-hydroxysuccinimide (NHS) (Sigma) was incubated with cells for 20 min at room temperature in PBS. The reaction was quenched with TBS for 15 min and cells were lysed in lysis buffer (TBS, 1% Triton X-100, 1% NP-40, 2 mM EDTA, 1 mM PMSF and Complete protease inhibitor mixture from Roche Molecular Biochemicals). Cell lysates were immunoprecipitated with anti-syndecan-3 antibodies (Nolo et al., 1995) and resolved on 7.5% SDS-PAGE. Autoradiography was performed with BAS1500 (Fuji). For heparinase III or PI-PLC treatment cells were incubated with 10 mU/ml heparinase III or with 1 U/ml PI-PLC, respectively for one hour at 37° C., 5% $CO_2$ before $^{125}$I-GDNF addition.

GDNF, NRTN and ARTN Interact with Heparin and HSPG Syndecan-3

The interaction between GDNF and syndecan-3 in cellular context was studied using the rat glioma C6 cell line, which expresses syndecan-3 (Kinnunen et al., 1998). Chemical cross-linking of $^{125}$I-GDNF to C6 cells followed by immunoprecipitation with syndecan-3 antibodies revealed specific interaction of GDNF and syndecan-3 on the cell surface (FIG. 2B). A high molecular weight complex revealed by autoradiography represents the GDNF complex with syndecan-3 oligomer. The interaction was displaced by excess of unlabelled (cold) GDNF or HB-GAM, another syndecan-3-specific ligand. Addition of 1 μg/ml of heparin, or removing HS chains by heparinase III treatment, abolished $^{125}$I-GDNF binding to syndecan-3 almost completely (FIG. 2B), confirming the involvement of HS chains in the interaction. To exclude the possibility of GPI-anchored GFRα1 involvement in the GDNF interaction with syndecan-3 on the cell surface we treated C6 cells with phosphatidylinositol-specific phospholipase C (PI-PLC). This treatment had no significant effect on $^{125}$I-GDNF binding to syndecan-3, indicating that GFRα1 is not required for the GDNF-syndecan-3 complex formation. In addition, the data on PI-PLC treatment indicate that other cell surface HSPGs, GPI-linked glypicans, are not involved in the interaction. These results allowed us to conclude that GDNF, ARTN and NRTN, but not PSPN, bind heparan sulfates and to syndecan-3 with high affinity, and that interaction between GDNF and syndecan-3 occurs through the HS chains of the proteoglycan.

Example 6

Separation of Membrane-Bound and ECM-Bound Protein Fractions of Mouse Organs

Postnatal day (P) 9 mouse brains and kidneys were dissociated in 1.5 ml of 10 mM Tris-HCl pH 7.5 (containing Complete protease inhibitor mix, 1 mM EDTA and 1 mM PMSF) by passing them through a 20 G needle on ice. After 10 min incubation on ice, insoluble material was spun down at 13000 rpm in a tabletop centrifuge for 60 min at +4° C. The supernatant was collected and labeled as the ECM fraction. The pellet, the cellular fraction, was dissolved in PBS with 1% NP-40 for 30-60 min on ice and centrifuged at 13000 rpm for 90 min at +4° C. The supernatant was collected and labeled as the membrane fraction. Volumes in both ECM and membrane fractions were equalized. Fractions were separated on 15% SDS-PAGE and western blots were stained either with GDNF antibodies (Santa-Cruz Biotechnology, Inc.) or with HB-GAM antibodies (Rauvala, 1989). Anti-rabbit horseradish peroxidase-conjugated secondary antibodies (Amersham) were used for the primary antibody detection. For imaging chemiluminescence LAS-3000 (Fuji) was used.

Example 7

Immunohistochemistry of Embryonic Kidney

Mouse E15 embryos were fixed with Bouin fixative and 8 μm thick sagittal sections were incubated overnight at +4° C. with mouse anti-GDNF (G90, Amgen) or with rabbit anti-HB-GAM antibodies (Rauvala, 1989) at 10 μg/ml and 3 μg/ml respectively. To detect primary antibodies the secondary goat Alexa488-conjugated anti-mouse and Alexa568-conjugated anti-rabbit antibodies (Molecular Probes) were used at 1:200 dilutions. Immunostained sections were photographed with a 20x objective on Zeiss Axioplan 2 fluorescent microscope (Zeiss).

GDNF Localization in the ECM and GFL-Induced Cell Spreading

Immobilized and diffusible molecules differentially regulate neuronal development and maintenance. It is generally thought that most neurotrophic factors, including GFLs, act as diffusible, soluble proteins. On the contrary, the ECM molecule HB-GAM signals through syndecan-3 only as an immobilized, matrix-bound protein and is not active as a soluble (diffusible) protein at physiological concentrations (Raulo et al., 1994, Kinnunen et al., 1998). Intriguingly, the ability of heparin-binding GFLs to interact with HSPGs raises the question whether the GFLs are bound to ECM in the tissue and, if so, does such binding affect their biological activity.

Figure 3:
Figure 3:
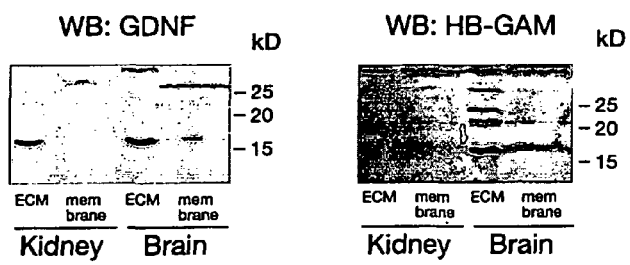

To answer this question we used embryonic kidney where GDNF is abundant and can be efficiently visualized. Immunohistochemical staining of mouse embryonic day (E) 15 kidney revealed that GDNF predominantly localizes to the ECM and plasma membrane (FIG. 3A). The pattern of GDNF localization is similar to that of the ECM molecule HB-GAM. To independently confirm the immunohistochemical data on GDNF localization to ECM, we performed biochemical fractionation of juvenile mice tissues followed by Western blotting, using HB-GAM as a marker for brain ECM. We found GDNF in the ECM fraction of postnatal brain and kidney (FIG. 3B). Most likely, abundant GDNF localization in the ECM can be explained by GDNF binding to the matrix HSPGs. In the brain, also the extracellular domain of syndecan-3 could be GDNF binding partner, as it can be released into ECM by specific protease cleavage (Reizes et al., 2001).

Figure 4:
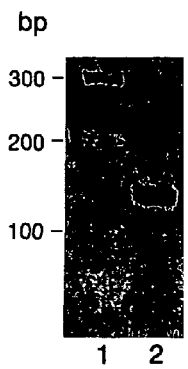
Figure 4:
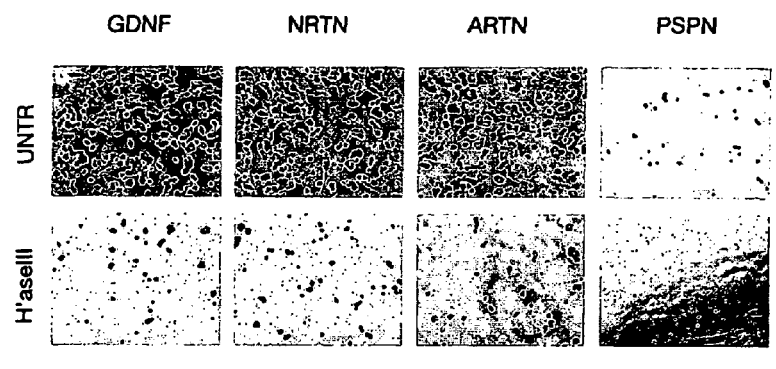
Figure 4:
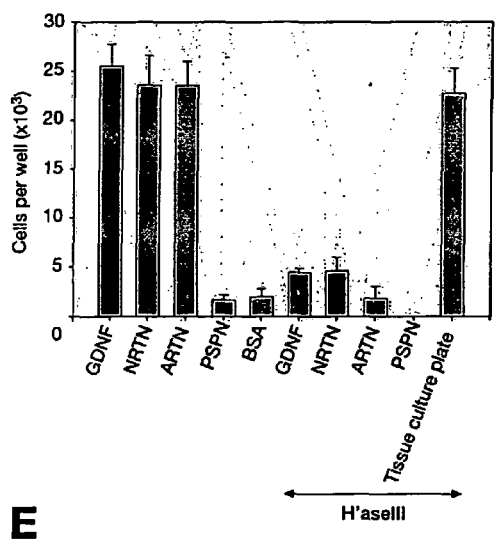
Figure 4:
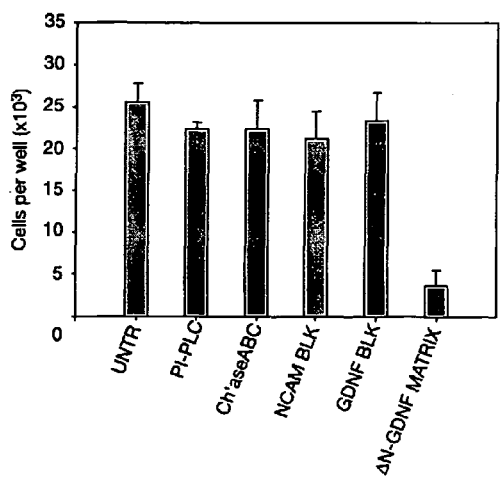
Figure 4:

To test the biological effects of immobilized GFLs we took advantage of human neuroblastoma cell line SHEP, which does not express RET but expresses the GDNF co-receptor GFRα1 (Poteryaev et al., 1999). SHEP cells also express syndecan-3 (FIG. 4A). Immobilized on plastic microplate GDNF, NRTN and ARTN, but not PSPN, induced adherence and spreading of SHEP cells (FIG. 4B, 4D). Spreading on immobilized GFLs involve 60-80% of the cells (FIG. 4B, 4C, 1D) and occurs within 10-20 minutes after settling. Spreading on immobilized GDNF is accompanied by actin rearrangement and stress fiber formation.

In order for SHEP cells to spread successfully on immobilized GFLs, HSPGs are required, since heparinase III treatment almost completely abolished cell attachment and spreading (FIG. 4B, 4D). Heparinase III had no effect on SHEP cell adhesion and spreading in uncoated tissue culture plates (FIG. 4D), indicating that the cellular machinery responsible for the observed adherence was not affected, and that the enzyme specifically disrupts the HS-GFL interactions. SHEP cells failed to adhere and spread on PSPN or BSA, which are precisely the proteins lacking affinity for HS. Treatment of SHEP cells with PI-PLC (FIG. 4C) did not affect their attachment and spreading, while it did affect soluble GDNF-induced RET-independent MAPK activation in SHEP cells via GFRα1. Soluble GDNF has been shown to induce MAPK activation in SHEP cells via GFRα1 in a RET-independent manner (Poteryaev et al., 1999). PI-PLC treatment almost completely blocked soluble GDNF-induced MAPK phosphorylation (data not shown). These results show a GFRα1-independent mechanism for immobilized GFL signaling. To further evaluate the role of GFRα1 and RET in immobilized GDNF-induced cell spreading, we preincubated the GDNF-coated plate and the SHEP cells with GDNF function-blocking antibodies. These antibodies prevent GDNF binding to GFRα1/RET, but do not affect GDNF binding to HS of syndecan-3 as they bind to the central part of GDNF (Xu et al., 1998). Neither of these treatments nor NCAM function-blocking antibodies had any effect on attachment and spreading of SHEP cells induced by immobilized GDNF (FIG. 4C). Adherence of SHEP cell to GDNF is also independent of another polysaccharide: glycosaminoglycan chondroitin sulfate, since it was not affected by the chondroitin sulfate lyase ABC treatment (FIG. 4C). Since SHEP cells do not express RET, we conclude that their attachment and spreading on immobilized GDNF, ARTN or NRTN does not require any conventional GFL receptors.

To confirm the involvement of HSPG, we generated a GDNF mutant that lacks 38 N-terminal amino acids (ΔN-GDNF) and does not bind to heparin (FIG. 9C). The N-terminal deletion does not significantly affect the ability of soluble ΔN-GDNF to activate the conventional GFRα1/Ret receptor complex (FIG. 9A and Eketjäll et al., 1999). In previously reported neurite outgrowth assays using dorsal root ganglia neurons (Paveliev et al., 2004), the soluble ΔN-GDNF mutant was shown to be biologically active (FIG. 9B). However, immobilized ΔN-GDNF failed to induce attachment and spreading of SHEP cells (FIG. 4C), which further confirms the involvement of HSPGs in the interaction with immobilized GDNF. These results further suggest that GDNF has two modes of action: as a diffusible, free protein activating GFRα1/RET receptors and as an immobilized, matrix-bound protein activating syndecan-3.

The present invention supports the notion that GDNF is localized predominantly in the ECM and cell membrane. Interaction with matrix HSPGs could dramatically change the properties and distribution of the heparin binding GFLs. By analogy with other heparin binding proteins, ECM could be the local store for GFL, participate in generation of GFL gradients thus determining their precise spatio-temporal positioning, protect GFLs from proteolysis (Hynes, 1999), or concentrate and present GFLs to their conventional GFRα/RET receptors (Sariola and Saarma, 2003).

Example 8

Cell Adhesion Assay

Cell adhesion assays were essentially performed as described elsewhere (Weinacker et al., 1994). To prepare protein-coated surfaces the protein of interest (10 µg/ml in PBS) was applied to 96-well ELISA (Greiner) plates or to glass cover slips for 12-18 hours at +4° C. After incubation, the surfaces were washed with PBS and blocked with 1% globulin-free BSA for two hours. Some GDNF coated surfaces were incubated with 20 µg/ml of G-90 (Amgen) GDNF function-blocking antibodies (Xu et al., 1998) for 2 hours at room temperature.

Subconfluent SHEP cells were harvested in PBS supplemented with 10 mM EDTA for 5 min at 37° C. Cells were washed with incubation buffer (RPMI 1640, 0.2% BSA, 15 mM HEPES pH 7.2) and 10000-40000 cells/well plated on the protein coated surface. Plates were centrifuged for 5 min at 10 g and incubated for one hour at 37° C. in 5% $CO_2$. After incubation cells were washed with PBS, fixed with methanol supplemented with crystal violet for 15 min at room temperature and washed again with PBS. The remaining cells were counted using a Leica DMIRB inverted microscope with 10× objective in 5 fields per well.

Some cells were pretreated with heparinase III, PI-PLC (see above), 0.3 U/ml chodroitinase ABC for one hour at 37° C., 5% $CO_2$, or with 20 µg/ml of NCAM blocking antibodies (AB5032, Chemicon Inc.) for 15-30 min on ice.

After one hour of incubation in serum-free medium unattached cells were removed by washing. The remaining cells were stained and counted on Leica DMIRB inverted microscope with a 10× objective in 5 fields per well and the resulting cell number was calculated for the whole well.

Live SHEP cells spreading on immobilized GDNF were imaged for 20 minutes using the Till imaging system with an Imago-QE digital camera (Till Photonics) equipped with heating (+37° C.) and CO$_2$ supply (5%) chambers.

Example 9

Src Kinase Phosporylation Assay

SHEP cells from 10-cm plates were harvested as described above and plated on GDNF-coated 35-mm Petri dishes. Cells were allowed to sediment for 10 min at room temperature and then transferred to 37° C. for additional 15 min. Cells were lysed in the lysis buffer (TBS, 1% Triton X-100, 0.5% deoxycholic acid, 0.1% SDS, 10% glycerol, 1 mM Na$_3$VO$_4$, 1 mM PMSF and Complete protease inhibitor mixture). Lysates were analyzed on 10% SDS-PAGE and western blots were stained with anti-pY$^{418}$Src or anti-pp60Src antibodies (Biosource). Some cells were pretreated with heparinase III or PI-PLC.

Example 10

Isolation and Characterization of Heparin Binding-Deficient GDNF Mutant

The sequence encoding residues 39-134 of mature human GDNF and N-terminal FLAG tag was subcloned into the pFASTBAC1 (Gibco-BRL)-based baculovirus transfer vector pK503.9 (Leppänen et al., 2004). For the baculoviral infection we used Sf9 insect cells grown in serum-free SF900II (Invitrogen) medium supplemented with 50 mg/ml gentamycin (Sigma) at +28° C. At 3 days postinfection of Sf9 cells the soluble, secreted N-terminal truncated GDNF (ΔN-GDNF) was produced at 0.5-1 mg/L concentration. ΔN-GDNF was purified from culture supernatants by anti-FLAG M1 affinity chromatography (Sigma) followed by cation exchange chromatography on UnoS (BioRad) column. The purity of the GDNF proteins was tested on 15% SDS-PAGE.

RET phosphorylation assay was done as described earlier (Leppänen et al., 2004). Neurite formation in cultured dorsal root ganglion neurons was tested in the presence of ΔN-GDNF or wtGDNF as described previously (Paveliev et al., 2004).

Immobilized GDNF Signaling Via Syndecan-3 Activates Src Kinases

Immobilized GDNF induces HSPG-dependent activation of Src family kinases (SFK) in SHEP cells as this activation is abolished by heparinase III treatment, and does not occur on immobilized ΔN-GDNF (FIG. 4E). However, SFK activation is GFRα1 independent, as shown by the lack of signaling inhibition by phosphatidylinositol-specific phospholipase C (PI-PLC) (FIG. 4E). Pretreatment of SHEP cells with the specific and non-toxic SFK inhibitor SU6656 (Paveliev et al., 2004) diminished their spreading on immobilized GDNF (FIG. 10A) but did not impair their adherence. Similar results were obtained with cells infected with a dominant-negative Src-kinase adenovirus (FIG. 10B), indicating that syndecan-3-mediated SFK activation is required for SHEP cell spreading induced by immobilized GDNF, but not for their attachment. These results are compatible with the syndecan-3-mediated signaling that requires HS chains and regulates cytoskeleton through the cortactin-SFK pathway (Rauvala et al., 2000).

Example 11

Neurite Outgrowth Assay in Rat Hippocampal Neurons

Hippocampi were dissected from E17 embryonic rat brains under the microscope and transferred to the preparation media (HBBS without Ca$^{2+}$ and Mg$^{2+}$ supplemented with 1 mM sodium pyruvate (Gibco) and buffered by 10 mM Hepes pH 7.2), then partially digested by papain and triturated in the preparation media supplemented with DNase I. Cells were washed with HBBS containing Ca$^{2+}$ and Mg$^{2+}$ and transferred to the growth media (Neurobasal media with B27 supplement, 2 mM L-glutamine, 25 µM glutamic acid and penicillin and streptomycin (Gibco)). For enzymatic treatments neurons were kept in the growth media supplemented with 0.2% BSA at +37° C. for one hour. After the treatment cells in the same media were seeded on the protein-coated cover slips (see above) and after 10 min, the media was changed for B27-free media. Neurons were incubated at +37° C., 5% CO$_2$ for 18 hours.

For immunocytochemistry neurons were washed with PBS and fixed with 4% PFA, permeabilized with 0.1% Triton X-100 and stained with rabbit polyclonal antiserum to Protein Gene Product 9.5 (Affiniti), neuron-specific Class III tubulin-βIII clone Tuj1 antibodies (BABCO) or with antibodies against the neurofilament triplet, 13AA8 (Arumäe et al., 1993). Secondary antibodies were goat anti-rabbit or anti-mouse Alexa488-conjugated (Molecular Probes).

The immunostained cultures were viewed using the ×20 objective of a Zeiss Axioplan 2 fluorescent microscope (Zeiss). Neurons with at least two times longer than cell body diameter processes were considered process-bearing. Three cover slips were used in parallel and 100 neurons per cover slip were counted. Results were derived from 3 to 5 independent experiments.

Immobilized GDNF Induces Neurite Outgrowth Via Heparan Sulfate Proteoglycan

Cell spreading is a crucial step in many biological processes including cell migration and neurite outgrowth. Soluble GFLs induce neurite outgrowth in a variety of neurons in vitro. In order to find out whether syndecan-3 interaction with immobilized GDNF is important for these processes, we used rat embryonic (E17) hippocampal neurons, which express syndecan-3 (Raulo et al., 1994; Lauri et al., 1999) and lack RET (Trupp et al., 1997). When grown on HB-GAM substrate, these neurons extend numerous neurites with prominent syndecan-3 localization in varicosities and growth cones (Raulo et al., 1994). In addition, immobilized GDNF stimulated neurite outgrowth in E17 hippocampal neurons (FIG. 5A). Neurite outgrowth quantification showed that the process was affected neither by PI-PLC treatment (FIG. 5C) nor by NCAM function-blocking antibodies (data not shown), excluding involvement of conventional receptors. The number of neurite-bearing neurons was significantly lower after treatment of cells with heparinase III, and neurons failed to form processes on non-heparin binding substrates ΔN-GDNF, PSPN and BSA (FIG. 5B, 5C), confirming the role of HS chains in the interaction. Likewise, the SFK inhibitor SU6656 prevented neurite outgrowth (FIG. 5C). Soluble GDNF added to neurons grown on BSA-matrix failed to induce neurites. Since both ΔN-GDNF and wtGDNF are basic proteins, we suggest that the observed neurite outgrowth is not attributed to the electrostatic properties of the surface and is specific for the heparin-binding tail of GDNF. We also conclude that the interaction between syndecan-3 and immobilized GDNF induces neurite formation in rat embryonic hippocampal neurons through SFK activation. Behavioral testing of the syndecan-3-deficient mice and GDNF heterozygous mice revealed impaired performance in tasks assessing hippocampal functioning (Gerlai et al., 2001, Kaksonen et al., 2002), suggesting genetic interaction between these two molecules.

Example 12

Cortical Neurons Migration Assay

Cortical lobes from E15 mouse brains were dissected under a stereomicroscope and dissociated using a 20 G needle and a syringe in DMEM containing 10% FCS. The cortical preparation was spun down at 1000 rpm for 5 min and the pellet was washed with culture medium containing serum. The pellet was carefully resuspended and the preparation was allowed to sediment for five more minutes before the cleared supernatant was collected. The cells in the supernatant were allowed to recover in serum-containing DMEM for 30-60 min. Recovered cells were washed once with the assay medium (DMEM with 10 mg/ml BSA, L-glutamine and antibiotics) and resuspended in the same medium.

Transwell filters (Costar) with 12-μm pore size or polycarbonate filters saturated with 100 μg/ml poly-L-lysine were coated with GDNF or ΔN-GDNF in 1 μM, 10 μM and 100 μM concentrations overnight at 4° C. and equilibrated with assay medium 30 min in +37° C. incubator prior to use. The spontaneous and random migratory activity of neural cells was controlled with uncoated filters.

Embryonic cortical cells were plated on the filters at 150000 cells per filter and left to migrate for 16 hours. Wild type embryonic cortical cells were used to examine the migration-inducing potential of GDNF and ΔN-GDNF. Syndecan-3 knockout mice cortical cells were used to determine the amount of migration to GDNF in the absence of syndecan-3. The filters were fixed with methanol for 20 min, stained with 1% toluidine blue for 20 min and washed with PBS several times. After the last wash the non-coated sides of the filters were scrubbed clean with cotton sticks and the filters were left to dry. The number of cells that had migrated to the coated surface of the filters was calculated using the inverted light microscope Olympus IX71. In this assay, syndecan-3-deficient neurons and wild type neurons migrated equally well when stimulated by laminin, suggesting that the general migratory systems are intact in these knockout neurons (data not shown).

Syndecan-3 Activation by GDNF Drives Migration of Embryonic Cortical Neurons

Tangential migration of cortical GABAergic neurons during embryonic development depends on GDNF, although cortical neurons lack RET and NCAM (Pozas and Ibáñez, 2005). In the transfilter cell migration assay, GDNF stimulated massive migration of embryonic cortical cells compared to the tissue culture-treated adhesive surface or the polycationic filter surface (FIG. 6A). In contrast, ΔN-GDNF did not induce migration in this assay. Likewise, GDNF-stimulated migration of syndecan-3-deficient (Reizes et al., 2001) embryonic cortical neurons was strongly impaired (FIG. 6A). Interestingly, the highest concentration of GDNF could also stimulate migration of the knockout neurons, indicating the potential involvement of the GFRα1 receptor (Pozas and Ibáñez, 2005).

Furthermore, the density of GABA-immunopositive cells was significantly lower in layers II-IV of dorso-medial cortex (DMC) of syndecan-3-deficient mice (FIG. 6B, 6C). DMC is the most distant area along the tangential migration route from the place of interneuron origin. Cortical areas proximal to the source of interneurons did not show any clear difference in the density of GABAergic neurons. The data provide direct evidence that GDNF signaling via syndecan-3 is important for the migration of embryonic cortical neurons.

Brain development is remarkably dependent on HSPG functioning. Neural-specific conditional knockout of EXT1, the enzyme that catalyzes HS polymerization, showed that this protein is vital for brain patterning and axon scaffold formation in the forebrain (Inatani et al., 2003). HSPG were shown to modulate the activity of many growth factors, but growth factors have never been demonstrated to signal via HSPG. Recent evidence (Pozas and Ibáñez, 2005) demonstrated that GDNF is also important for the migration and development of cortical neurons, which lack the canonical GFL receptors RET and NCAM.

During cerebral cortex formation, inhibitory GABAergic interneurons originate mainly from the medial ganglionic eminence (MGE) and then migrate tangentially into the developing cortical layers (FIG. 6C). Recently, mouse cortical GABAergic neurons were shown to migrate along the GDNF gradient from the MGE towards the cortex. These neurons are devoid of RET and NCAM, and so it has been suggested that an alternative GDNF receptor system drives their migration (Pozas and Ibáñez, 2005). Detailed analysis by Pozas and Ibáñez (2005) demonstrated that GDNF and GFRα1 knockout animals have significantly fewer GABAergic neurons in their cortex, whereas mice lacking RET and NCAM have the normal number of GABAergic cortical neurons. Consequently, GDNF was shown to be the chemoattractant factor for GABAergic cortical neurons, which acts via a novel RET- and NCAM-independent pathway.

Example 13

Estimation of GABAergic Neurons in the Mouse Cortex.

Coronal paraffin sections (5 mm thick) from adult syndecan-3 wild type and knockout brains were dewaxed and hydrated. Antibodies against GABA (1 μg/ml, Chemicon) were diluted in PBS containing 2% BSA and 0.3% Triton X-100. The sections were incubated with the antibody solution overnight and biotinylated secondary antibodies were used to detect the immunostaining signal. For quantifications the required brain areas (dorso-medial, dorso-lateral and lateral cortices) were photographed at 63× magnification with Zeiss AxioCam camera mounted in AxioPlan microscope. Cell density estimates from photographs were made by the selector-method (Everall et al., 1997) using ImageJ software (NIH, http://rsb.info.nih.gov/ij/index.html).

Example 14

The Screening of Molecules Capable of Displacing GDNF from Heparan Sulfates Thus Increasing GDNF Biodistribution The biodistribution of GDNF is increased by interfering with the interaction between GDNF and syndecan-3, and thereby the released GDNF can act via the other known receptors The scintillation proximity assay (SPA) technology (Amersham) was used to assay the ability of the low molecular weight molecule (namely low molecular weight heparin from Sigma) to displace tritium labeled heparin from GDNF.

Small beads filled with scintillation liquid are covalently linked with anti-mouse antibodies that can capture mouse anti-FLAG-tag antibodies. In turn, GDNF that we produced by ourselves has a FLAG-tag on its N-terminus. Thus, GDNF is in close proximity to the scintillation beads. The tritium labeled high molecular weight heparin (a kind gift from Ulf Lindahl, Sweden) is administered in the surrounding solution. Labeled heparin binds GDNF, which is sitting on scintillation beads and induces light that is detected. The labeled heparin which is unbound by GDNF is too far away from the beads and does not substantially contribute to the signal. This assay can be easily adopted to high-throughput format.

To test the ability of small molecules to displace heparin or heparan sulfates from GDNF they are simply mixed at different concentrations with the labeled heparin and the decrease of the signal is monitored. It does positively correlate with the concentration of the cold heparin. We did it in our study with low molecular weight heparin and got IC50 of approximately 10 nM, which correlates with other binding data (FIG. 11).

Example 15

The Screening of the Molecules Mimicking GDNF, NRTN and ARTN that can Activate Syndecan-3 Thus Promoting Neurite Outgrowth, Migration and Neuronal Survival.

Syndecan-3 is activated and mediates the cell spreading and neurite outgrowth via Src family kinase (SFK) activation.

The molecules that bind to heparan sulfate chains of the syndecan-3 and induce its oligomerization are searched. This leads to syndecan-3 activation. These molecules should be positively charged and relatively big for instance polycations like spermidin.

Alternatively, it is possible to screen for the molecules that bind to the intracellular domain of syndecan-3 and recruit adaptor proteins that syndecan-3 uses to signal into the cell, for instance CASK, Src, etc.

TABLE 1

Analysis of GDNF family ligand binding to heparin. GFLs interaction with heparin-BSA cuvette.

| Ligand | $k_a$ (×10$^{-5}$) (M$^{-1}$s$^{-1}$) | $k_{dis}$ (s$^{-1}$) | $K_d = k_{dis}/k_a$ (nM) | $K_d$ (equilibrium) (nM) |
|---|---|---|---|---|
| GDNF | 3.7 | 0.017 | 47.3 ± 9.9 | 51.3 ± 3.6 |
| NRTN | 3.2 | 0.018 | 59.4 ± 6.2 | 47.0 ± 7.0 |
| ARTN | 0.09 | 0.0013 | 148 ± 39 | 187 ± 34 |
| PSPN | 0.87 | 0.093 | 1072 ± 118 | >1000 |

TABLE 2

Analysis of GDNF family ligand binding to heparin. Heparin interaction with GFLs cuvette.

| Ligand | $k_a$ (×10$^{-5}$) (M$^{-1}$s$^{-1}$) | $k_{dis}$ (s$^{-1}$) | $K_d = k_{dis}/k_a$ (nM) | $K_d$ (equilibrium) (nM) |
|---|---|---|---|---|
| GDNF | 15 | 0.034 | 22.7 ± 2.7 | 12.3 ± 3.4 |
| NRTN | 1.9 | 0.022 | 114 ± 44 | 23.7 ± 7.7 |
| ARTN | 8.0 | 0.042 | 44.7 ± 12.3 | 13.0 ± 3.9 |
| PSPN | 0.02 | 0.064 | (29.1 ± 7.3) × 10$^3$ | (11.1 ± 4.5) × 10$^3$ |

TABLE 3

Analysis of GDNF family ligand binding to syndecan-3. Syndecan-3 ectodomain interaction with GFLs cuvette.

| Ligand | $k_a$ (×10$^{-5}$) (M$^{-1}$s$^{-1}$) | $k_{dis}$ (s$^{-1}$) | $K_d = k_{dis}/k_a$ (nM) | $K_d$ (equilibrium) (nM) |
|---|---|---|---|---|
| GDNF | 13 ± 2 | 0.015 ± 0.004 | 11.5 ± 2.9 | 12.0 ± 3.0 |
| NRTN | 7.5 ± 1.6 | 0.021 ± 0.004 | 26.3 ± 5.5 | 28.5 ± 9.7 |
| ARTN | 6.3 ± 0.7 | 0.034 ± 0.002 | 53.9 ± 5.9 | 21.2 ± 4.1 |
| PSPN | — | — | — | >70 |

Binding was analyzed using IAsys cuvettes with immobilized heparin-BSA or GFLs. The dissociation constant $K_d$ was determined from dynamics of association and dissociation ($K_d = k_{dis}/k_a$), or from equilibrium response R (R= ($R_{max}$*C)/($K_d$+C), where C is ligand concentration).

TABLE 4

Effect of desulfation on the interaction between GDNF and heparin assayed by SPR.

| | $K_{d1}$ (nM)[a] | $K_{d2}$ (µM)[a] | IC50 (ng/ml)[b] |
|---|---|---|---|
| Heparin | 9.5 ± 0.5 | — | 0.06 |
| 2-O-desulfated heparin[c] | 35.4 ± 7.5 | 9.5 ± 3.3 | 4.3 |
| 6-O-desulfated heparin[c] | 36.3 ± 4.6 | 18.1 ± 4.0 | 1.3 |
| N-desulfated heparin[c] | 29.1 ± 6.4 | 11.4 ± 3.5 | 2.3 |

[a]apparent dissociation constants were calculated from equilibrium response (R) for direct binding of heparin or desulfated heparin to GDNF cuvette by fitting equation R = ($R_{max}$ * C)/($K_{d1}$ + C) for heparin or R = ($R_{max1}$ * C)/($K_{d1}$ + C) + ($R_{max2}$ * C)/($K_{d2}$ + C) for desulfated heparins.
[b]Increasing concentrations of heparin or desulfated heparins were used to compete out GDNF binding to heparin-BSA cuvette and to determine the IC50.
[c]Presence of higher affinity component ($K_{d1}$ of 30–40 nM) for all desulfated heparins could be a result of incomplete desulfation and/or presence of residual sites with high affinity for GDNF.

REFERENCES

Airaksinen, M. S., and Saarma, M. (2002). The GDNF family: signaling, biological functions and therapeutic value. Nat. Rev. Neurosci. 3:383-394.

Arumäe, U., Pirvola, U., Palgi, J., Kiema, T. R., Palm, K., Moshnyakov, M., Ylikoski, J., and Saarma, M. (1993). Expression patterns of neurotrophin and their receptor mRNAs in the rat inner ear. Hear. Res. 65:69-78.

Barnett, M. W., Fisher, C. E., Perona-Wright, G., and Davies, J. A. (2002). Signaling by glial cell line-derived neurotrophic factor (GDNF) requires heparan sulphate glycosaminoglycan. J. Cell Sci. 115:4495-4503.

Bullock, S. L., Fletcher, J. M., Beddington, R. S., and Wilson, V. A. (1998). Renal agenesis in mice homozygous for a gene trap mutation in the gene encoding heparan sulfate 2-sulfotransferase. Genes Dev. 12:1894-1906.

Cardin, A. D., and Weintraub, H. J. (1989). Molecular modeling of protein-glycosaminoglycan interactions. Arteriosclerosis 9:21-32.

Eketjäll, S., Fainzilber, M., Murray-Rust, J., and Ibáñez, C. F. (1999). Distinct structure elements in GDNF mediate binding to GFR alpha 1 and activation of the GFR alpha 1-c-Ret receptor complex. EMBO J. 18:5901-5910.

Everall, I. P., DeTeresa, R., Terry, R., Masliah, E. (1997). Comparison of two quantitative methods for the evaluation of neuronal number in the frontal cortex in Alzheimer disease. J. Neuropathol. Exp. Neurol. 56:1202-1206.

Gerlai, R., McNamara, A., Choi-Lundberg, D. L., Armanini, M., Ross, J., Powell-Braxton, L., and Phillips, H. S. (2001). Impaired water maze learning performance without altered dopaminergic function in mice heterozygous for the GDNF mutation. Eur. J. Neurosci. 14:1153-1163.

Gill, S. S., Patel, N. K., Hotton, G. R., O'Sullivan, K., McCarter, R. Bunnage, M., Brooks, D. J., Svendsen, C. N., and Heywood, P. (2003). Direct brain infusion of glial cell line-derived neurotrophic factor in Parkinson disease. Nat. Med. 9:589-595.

Hamilton, J. F., Morrison, P. F., Chen, M. Y., Harvey-White, J., Pernaute, R. S., Phillips, H., Oldfield, E., and Bankiewicz, K. S. (2001). Heparin coinfusion during convection-enhanced delivery (CED) increases the distribution of the glial-derived neurotrophic factor (GDNF) ligand family in rat striatum and enhances the pharmacological activity of neurturin. Exp. Neurol. 168:155-161.

Henderson, C. E., Phillips, H. S., Pollock, R. A., Davies, A. M., Lemeulle, C., Armanini, M., Simmons, L., Moffet, B., Vandlen, R. A., and Simpson, L. C. (1994). GDNF: a potent survival factor for motoneurons present in peripheral nerve and muscle. Science 266:1062-1064.

Hynes, R. O. (1999). Cell adhesion: old and new questions. Trends Cell Biol. 9:M33-M37.

Inatani., M., Irie, F., Plump, A. S., Tessier-Lavigne, M., and Yamaguchi, Y. (2003). Mammalian brain morphogenesis and midline axon guidance require heparan sulfate. Science 302:1044-1046.

Kaksonen, M., Pavlov, I., Voikar, V., Lauri, S. E., Hienola, A., Riekki, R., Lakso, M., Taira, T., and Rauvala, H. (2002). Syndecan-3-deficient mice exhibit enhanced LTP and impaired hippocampus-dependent memory. Mol. Cell. Neurosci. 21:158-172.

Kinnunen, A., Niemi, M., Kinnunen, T., Kaksonen, M., Nolo, R., and Rauvala, H. (1997). Heparan sulphate and HB-GAM (heparin-binding growth-associated molecule) in the development of the thalamocortical pathway of rat brain. Eur. J. Neurosci. 11:491-502.

Kinnunen, T., Kaksonen, M., Saarinen, J., Kalkkinen, N., Peng, H. B., and Rauvala, H. (1998). Cortactin-Src kinase signaling pathway is involved in N-syndecan-dependent neurite outgrowth. J. Biol. Chem. 273:10702-10708.

Lang, A. E., Gill S., Patel, N. K., Lozano, A., Nutt, J. G., Penn, R., Brooks, D. J., Hotton, G., Moro, E., Heywood, P. et al. (2006). Randomized controlled trial of intraputamenal glial cell line-derived neurotrophic factor infusion in Parkinson disease. Ann. Neurol. 59:459-466.

Lauri, S. E., Kaukinen, S., Kinnunen, T., Ylinen, A., Imai, S., Kaila, K., Taira, T., and Rauvala, H. (1999). Regulatory role and molecular interactions of a cell-surface heparan sulfate proteoglycan (N-syndecan) in hippocampal long-term potentiation. J. Neurosci. 19:1226-1235.

Leppänen, V. M., Bespalov, M. M., Runeberg-Roos, P., Puurand, U., Merits, A., Saarma, M., and Goldman, A. (2004). The structure of GFRalpha1 domain 3 reveals new insights into GDNF binding and RET activation. EMBO J. 23:1452-1462.

Lin, L. F., Doherty, D. H., Lile, J. D., Bektesh, S., Collins, F. (1993). GDNF—a glial cell line-derived neurotrophic factor for midbrain dopaminergic-neurons. Science 260:1130-1132.

Lindahl, M., Poteryaev, D., Yu, L., Arumäe, U., Timmusk, T., Bongarzone, I., Aiello, A., Pierotti, M. A., Airaksinen, M. S., and Saarma, M. (2001). Human glial cell line-derived neurotrophic factor receptor alpha 4 is the receptor for persephin and is predominantly expressed in normal and malignant thyroid medullary cells. J. Biol. Chem. 276:9344-9351.

Nolo, R., Kaksonen, M., Raulo, E., and Rauvala, H. (1995). Co-expression of heparin-binding growth-associated molecule (HB-GAM) and N-syndecan (syndecan-3) in developing rat brain. Neurosci. Lett. 191:39-42.

Paratcha, G., Ledda, F., and Ibáñez, C. F. (2003). The neural cell adhesion molecule NCAM is an alternative signaling receptor for GDNF family ligands. Cell 113:867-879.

Paveliev, M., Airaksinen, M. S., and Saarma, M. (2004). GDNF family ligands activate multiple events during axonal growth in mature sensory neurons. Mol. Cell. Neurosci. 25:453-459.

Poteryaev, D., Titievsky, A., Sun, Y. F., Thomas-Crusells, J., Lindahl, M., Billaud, M., Arumae, U., and Saarma M. (1999). GDNF triggers a novel Ret-independent Src kinase family-coupled signaling via a GPI-linked GDNF receptor alpha 1. FEBS Lett. 463:63-66.

Pozas, E., and Ibáñez, C. F. (2005). GDNF and GFR alpha 1 promote differentiation and tangential migration of cortical GABAergic neurons. Neuron 45:701-713.

Raulo, E., Chernousov, M. A., Carey, D. J., Nolo, R., and Rauvala, H. (1994). Isolation of a neuronal cell surface receptor of heparin binding growth-associated molecule (HB-GAM). Identification as N-syndecan (syndecan-3). J. Biol. Chem. 269:12999-13004.

Rauvala, H. (1989). An 18-kd heparin-binding protein of developing brain that is distinct from fibroblast growth factors. EMBO J. 8:2933-2941.

Rauvala, H., Huttunen, H. J., Fages, C., Kaksonen, M., Kinnunen, T., Imai, S., Raulo E., and Kilpeläinen, I. (2000). Heparin-binding proteins HB-GAM (pleiotrophin) and amphoterin in the regulation of cell motility. Matrix Biol. 19:377-387.

Reizes, O., Lincecum, J., Wang, Z. H., Goldberger, O., Huang, L., Kaksonen, M., Ahima, R., Hinkes, M. T., Barsh, G. S., Rauvala, H., and Bernfield, M. (2001). Transgenic expression of syndecan-1 uncovers a physiological control of feeding behavior by syndecan-3. Cell 106:105-116.

Rickard, S. M., Mummery, R. S., Mulloy, B., and Rider C. C. (2003). The binding of human glial cell line-derived neurotrophic factor to heparin and heparan sulfate: importance of 2-O-sulfate groups and effect on its interaction with its receptor, GFR alpha 1. Glycobiology 13:419-426.

Sariola, H., and Saarma M. (2003). Novel functions and signaling pathways for GDNF. J. Cell Sci. 116:3855-3862.

Takano, R., Ye, Z., Ta, T-V., Hayashi, K., Kariya, Y., and Hara, S. (1998). Specific 6-O-desulfation of heparin. Carbohydr. Lett. 3:71-77.

Tanaka, M., Xiao, H. Y., and Kiuchi, K. (2002). Heparin facilitates glial cell line-derived neurotrophic factor signal transduction. Neuroreport 13:1913-1916.

Trupp, M., Belluardo, N., Funakoshi, H., and Ibáñez, C. F. (1997). Complementary and overlapping expression of glial cell line-derived neurotrophic factor (GDNF), c-ret protooncogene, and GDNF receptor-alpha indicates multiple mechanisms of trophic actions in the adult rat CNS. J. Neurosci. 17:3554-3567.

Weinacker, A., Chen, A., Agrez, M., Cone, R. I., Nishimura, S., Wayner, E., Pytela, R., and Sheppard, D. (1994). Role of the integrin alpha v beta 6 in cell attachment to fibronectin. Heterologous expression of intact and secreted forms of the receptor. J. Biol. Chem. 269:6940-6948.

Xu, R. Y., Pong, K., Yu, Y. B., Chang, D., Liu, S. Y., Lile, J. D., Treanor, J., Beck, K. D., and Louis, J. C. (1998). Characterization of two distinct monoclonal antibodies specific for glial cell line-derived neurotrophic factor. J. Neurochem. 70:1383-1393.

Zuckermann, R. N., Martin, E. J., Spellmeyer, D. C., Stauber, G. B., Shoemaker, K. R., Kerr, J. M., Figliozzi, G. M., Goff, D. A., Siani, M. A., Simon R. J., et al. (1994) Discovery of nanomolar ligands for 7-transmembrane G-protein-coupled receptors from a diverse N-(substituted)glycine peptoid library. J. Med. Chem. 37: 2678-85.

The invention claimed is:

1. An in vitro method for identifying a molecule, which interferes with the interaction between a glial cell-line derived neurotrophic factor family ligand (GFL) selected from the group consisting of glial cell line-derived neurotrophic factor (GDNF), neurturin (NRTN), artemin (ARTN), and combinations thereof, and a heparan sulfate proteoglycan (HSPG) selected from the group consisting of syndecan-3, oligomerized syndecan-3, and combinations thereof, by screening a library of molecules against a matrix anchored complex comprising at least one immobilized glial cell-line derived neurotrophic factor family ligand (GFL) and at least one heparan sulfate proteoglycan (HSPG), wherein the interfering molecule is isolated based on its capacity to replace a glial cell-line derived neurotrophic factor family ligand (GFL) in said anchored complex.

2. The method of claim 1, wherein the isolated purified anchored complex is present in a neuronal cell.

3. The method of claim 1, wherein the anchored complex is attached to a solid support.

4. The method of claim 1, wherein the glial cell-line derived neurotrophic factor family ligand (GFL) is selected from the group consisting of glial cell-line derived neurotrophic factor (GDNF), neurturin (NRTN), and artemin (ARTN).

5. The method of claim 1, wherein the heparan sulfate proteoglycan (HSPG) is syndecan-3.

6. The method of claim 1, wherein the heparan sulfate proteoglycan (HSPG) is oligomerized syndecan-3.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 1
atggccattg cttacctgg                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagcgcatgg ctgtctcaa                                                    19
```